(12) United States Patent
Adachi et al.

(10) Patent No.: US 11,226,321 B2
(45) Date of Patent: Jan. 18, 2022

(54) GAS SENSOR AND PROTECTIVE COVER

(71) Applicant: NGK INSULATORS, LTD., Aichi (JP)

(72) Inventors: Yosuke Adachi, Nagoya (JP); Takeshi Omori, Niwa-gun (JP)

(73) Assignee: NGK INSULATORS, LTD., Nagoya (JP)

(*) Notice: Subject to any disclaimer, the term of this patent is extended or adjusted under 35 U.S.C. 154(b) by 0 days.

(21) Appl. No.: 17/038,103

(22) Filed: Sep. 30, 2020

(65) Prior Publication Data

US 2021/0102928 A1    Apr. 8, 2021

(30) Foreign Application Priority Data

Oct. 3, 2019    (JP) .............................. JP2019-183073

(51) Int. Cl.
G01D 11/26 (2006.01)
G01N 33/00 (2006.01)
G01D 11/24 (2006.01)

(52) U.S. Cl.
CPC ....... G01N 33/0036 (2013.01); G01D 11/245 (2013.01); G01D 11/26 (2013.01)

(58) Field of Classification Search
CPC ... G01N 33/0036; G01D 11/245; G01D 11/26
See application file for complete search history.

(56) References Cited

U.S. PATENT DOCUMENTS

| | | | | |
|---|---|---|---|---|
| D884,523 S | * | 5/2020 | Seimori | ..................... D10/81 |
| 2008/0156644 A1 | | 7/2008 | Suzuki et al. | |
| 2016/0076919 A1 | | 3/2016 | Murakami et al. | |
| 2017/0363596 A1 | | 12/2017 | Adachi et al. | |
| 2021/0102915 A1 | * | 4/2021 | Takahashi | .......... G01N 27/4077 |
| 2021/0102926 A1 | * | 4/2021 | Adachi | .............. G01N 33/0009 |
| 2021/0102927 A1 | * | 4/2021 | Takahashi | .......... G01N 33/0009 |

FOREIGN PATENT DOCUMENTS

| | | |
|---|---|---|
| JP | 2008-164411 A | 7/2008 |
| JP | 2017-223620 A | 12/2017 |
| WO | 2014/192945 A1 | 12/2014 |

OTHER PUBLICATIONS

Unexamined U.S. Appl. No. 17/038,099, filed Sep. 30, 2020.
Unexamined U.S. Appl. No. 17/038,109, filed Sep. 30, 2020.
Unexamined U.S. Appl. No. 17/038,110, filed Sep. 30, 2020.

* cited by examiner

*Primary Examiner* — Jamel E Williams

(74) *Attorney, Agent, or Firm* — Mattingly & Malur, PC

(57) ABSTRACT

A gas sensor includes a sensor element, an inner protective cover having inside a sensor element chamber and having an element chamber inlet and an element chamber outlet, and an outer protective cover having an outer inlet and an outer outlet. A total cross-sectional area A [mm$^2$] of the outer inlet, a total cross-sectional area B [mm$^2$] of the element chamber inlet, a total cross-sectional area C [mm$^2$] of the element chamber outlet, and a total cross-sectional area D [mm$^2$] of the outer outlet satisfy B>A>C>D, a cross-sectional area ratio A/D is greater than a value of 2.0 and less than or equal to a value of 5.0, and A×B×C×D is greater than or equal to a value of 3000 and less than or equal to a value of 8500.

9 Claims, 10 Drawing Sheets

GAS SENSOR AND PROTECTIVE COVER

The present application claims priority from Japanese Patent Application No. 2019-183073 filed Oct. 3, 2019, the entire contents of which are incorporated herein by reference.

BACKGROUND OF THE INVENTION

1. Field of the Invention

The present invention relates to a gas sensor and a protective cover.

2. Description of the Related Art

Hitherto, a gas sensor that detects the concentration of predetermined gas, such as NOx and oxygen, in measurement-object gas, such as exhaust gas of an automobile, is known. For example, Patent Literature 1 describes a gas sensor including an outer protective cover, and a closed-end cylindrical inner protective cover disposed between the outer protective cover and a sensor element and covering a tip end of the sensor element. Patent Literature 1 describes the outer protective cover having a plurality of first outer gas holes into which measurement-object gas flows, and second outer gas holes from which measurement-object gas flows out. Patent Literature 1 describes that both the response of gas concentration detection and the heat retaining property of the sensor element are obtained by forming the shape of the inner protective cover in a predetermined shape. Patent Literature 2 describes that, in such a gas sensor, the response of gas concentration detection is further improved by setting a cross-sectional area ratio S1/S2, which is the ratio between a total cross-sectional area S1 of the first outer gas holes and a total cross-sectional area S2 of the second outer gas holes, to a value greater than 2.0 and less than or equal to 5.0.

CITATION LIST

Patent Literature

PTL 1: Pamphlet of International Publication No. 2014/192945
PTL 2: Japanese Unexamined Patent Application Publication No. 2017-223620

SUMMARY OF THE INVENTION

Incidentally, the response of gas concentration detection also varies depending on the flow speed of measurement-object gas that flows around a gas sensor, and it has been inconvenient that the response tends to decrease when the flow speed is low (for example, lower than 2 m/s). In addition, when the response is attempted to be increased, the heat retaining property may decrease.

The present invention is made to solve such inconvenience, and it is a main object to reduce a decrease in response at a low flow speed of measurement-object gas and to reduce a decrease in heat retaining property.

The present invention employs the following manner to achieve the above-described main object.

A gas sensor of the present invention includes:
a sensor element having a gas inlet port that introduces measurement-object gas and capable of detecting a specific gas concentration of the measurement-object gas having flowed in from the gas inlet port;

an inner protective cover having inside a sensor element chamber in which a tip end of the sensor element and the gas inlet port are disposed, and having one or more element chamber inlets that are inlets to the sensor element chamber and one or more element chamber outlets that are outlets from the sensor element chamber; and an outer protective cover disposed outside the inner protective cover and having one or more outer inlets that are inlets for the measurement-object gas from an outside and one or more outer outlets that are outlets for the measurement-object gas to the outside, wherein the outer protective cover and the inner protective cover form, as spaces between the outer protective cover and the inner protective cover, a first gas chamber that is at least part of a flow channel for the measurement-object gas between the one or more outer inlets and the one or more element chamber inlets and a second gas chamber that is at least part of a flow channel for the measurement-object gas between the one or more outer outlets and the one or more element chamber outlets and that does not directly communicate with the first gas chamber, and a total cross-sectional area A [mm$^2$] of the one or more outer inlets, a total cross-sectional area B [mm$^2$] of the one or more element chamber inlets, a total cross-sectional area C [mm$^2$] of the one or more element chamber outlets, and a total cross-sectional area D [mm$^2$] of the one or more outer outlets satisfy B>A>C>D, a cross-sectional area ratio A/D that is a ratio between the total cross-sectional area A and the total cross-sectional area D is greater than a value of 2.0 and less than or equal to a value of 5.0, and A×B×C×D that is a product of the total cross-sectional areas A to D is greater than or equal to a value of 3000 and less than or equal to a value of 8500.

In this gas sensor, measurement-object gas flowing around the gas sensor flows in from the one or more outer inlets of the outer protective cover and reaches the gas inlet port in the sensor element chamber through the first gas chamber and the one or more element chamber inlets. Measurement-object gas in the sensor element chamber flows out from the one or more outer outlets of the outer protective cover through the one or more element chamber outlets and the second gas chamber. At this time, when the cross-sectional area ratio A/D is greater than a value of 2.0, the flow rate of measurement-object gas flowing in from the one or more outer inlets tends to increase since the total cross-sectional area A is relatively large, and the flow of measurement-object gas that attempts to flow in (flow backward) from the one or more outer outlets tends to decrease since the total cross-sectional area D is relatively small. With this configuration, a space around the gas inlet port is easily replaced by measurement-object gas having flowed in. Therefore, the response of specific gas concentration detection improves. When the total cross-sectional area D is too small, the flow rate of measurement-object gas that flows out from the one or more outer outlets may decrease and, as a result, the response may decrease; however, when the cross-sectional area ratio A/D is less than or equal to a value of 5.0, such a decrease in response is reduced. Incidentally, when the flow speed of measurement-object gas is low, the flow rate of measurement-object gas that flows in from the one or more outer inlets is low, so the flow rate of measurement-object gas that flows into the sensor element chamber from the one or more outer inlets is low. In the case where the flow speed of measurement-object gas is low in this way, when the total cross-sectional areas A to D satisfy B>A>C>D, flow of measurement-object gas is smooth, most of measurement-object gas that flows in from the one or more outer inlets flows into the sensor element chamber, and most of measurement-object gas having flowed into the sensor element chamber flows out from the one or more outer outlets without flowing backward. In other words, when the total cross-sectional area B is greater than the total cross-sectional area A, most of gas having flowed in from the one or more outer inlets flows into the sensor element chamber through the one or more element chamber inlets, so the flow rate of measurement-object gas that flows into the sensor element chamber tends to increase. When the total cross-sectional area A is greater than the total cross-sectional area C, the flow rate of measurement-object gas that attempts to flow in (flow backward) from the one or more element chamber outlets tends to decrease. In addition, when the total cross-sectional area C is greater than the total cross-sectional area D, the flow rate of measurement-object gas that attempts to flow in (flow backward) from the one or more outer outlets tends to decrease. With this configuration, even when the flow speed of measurement-object gas is low, a space around the gas inlet port is easily replaced by measurement-object gas having flowed in. Therefore, even when the flow speed of measurement-object gas is low, it is possible to improve the response of specific gas concentration detection without increasing the total cross-sectional areas A to D of the outlets and inlets to such an extent that the heat retaining property decreases. In addition, when A×B×C×D that is the product of the total cross-sectional areas A to D is greater than or equal to a value of 3000, any one or more of A to D are not extremely small or all of A to D are not too small, so flow of measurement-object gas is smooth, and the response of specific gas concentration detection is improved. Furthermore, when A×B×C×D is less than or equal to a value of 8500, any one or more of A to D are not extremely large or all of A to D are not too large, so a decrease in heat retaining property is also reduced. In this way, with this gas sensor, it is possible to reduce a decrease in response at a low flow speed of measurement-object gas and to reduce a decrease in heat retaining property.

In the gas sensor of the present invention, the cross-sectional area ratio A/D is preferably greater than or equal to a value of 2.5, more preferably greater than or equal to a value of 3.0, and further more preferably greater than or equal to a value of 3.4. As the cross-sectional area ratio A/D increases, the response of specific gas concentration detection tends to improve.

In the gas sensor of the present invention, the total cross-sectional area A may be greater than or equal to 10 $mm^2$ or may be less than or equal to 30 $mm^2$. The total cross-sectional area B may be greater than or equal to 15 $mm^2$ or may be less than or equal to 50 $mm^2$. The total cross-sectional area C may be greater than or equal to 5 $mm^2$ or may be less than or equal to 15 $mm^2$. The total cross-sectional area D may be greater than or equal to 1.6 $mm^2$ or may be less than or equal to 10 $mm^2$.

In the gas sensor of the present invention, the outer protective cover may have a closed-end cylindrical shape and have a side portion and a bottom portion, and the one or more outer outlets may be not disposed at the side portion of the outer protective cover. When the one or more outer outlets disposed at the side portion of the outer protective cover are present, the response may change depending on the positional relation between the one or more outer outlets of the side portion and the flow direction of surrounding measurement-object gas. When, for example, the one or more outer outlets of the side portion are open toward an upstream side and parallel to the flow direction of measurement-object gas, measurement-object gas flowing therearound interferes with flow of measurement-object gas that attempts to flow out from the inside of the outer protective cover to the outside through the one or more outer outlets of the side portion, so the response tends to decrease. When a change in response due to such a positional relation between the one or more outer outlets of the side portion and the flow direction of surrounding measurement-object gas is large, the response may decrease depending on, for example, an orientation in which the gas sensor is attached. Because no outer outlet is disposed at the side portion, the influence on the response due to an orientation in which the gas sensor is attached is reduced. In this case, the one or more outer outlets may be disposed at least one of the bottom portion and an corner portion at a boundary between the side portion and the bottom portion. The one or more outer outlets may be disposed at only the bottom portion or may be disposed at only the corner portion.

In the gas sensor of the present invention, the inner protective cover may have a closed-end cylindrical shape and have a side portion and a bottom portion, and the one or more element chamber outlets may be not disposed at the bottom portion of the inner protective cover. The sensor element is less likely to be exposed to water when the sensor element is not disposed along a line extended from each of the one or more element chamber outlets, and a configuration in which the sensor element is not disposed along the line extended from each of the one or more element chamber outlets is easily realized when no element chamber outlet is disposed at the bottom portion of the inner protective cover.

In the gas sensor of the present invention, the inner protective cover may form the one or more element chamber inlets such that, where a direction from a rear end of the sensor element toward the tip end of the sensor element is a tip end direction, an element-side opening that is an opening adjacent to the sensor element chamber of each of the one or more element chamber inlets is open in the tip end direction. With this configuration, it is possible to reduce a situation in which measurement-object gas, flowing out from the element-side opening, perpendicularly strikes the surface (surface other than the gas inlet port) of the sensor element and to reduce a situation in which measurement-object gas passes along the surface of the sensor element over a long distance and then reaches the gas inlet port. Thus, it is possible to further suppress a decrease in the heat retaining property of the sensor element. In addition, a decrease in the heat retaining property of the sensor element is suppressed by adjusting the orientation of the opening of the element-side opening, and the flow rate or flow speed of measurement-object gas inside the inner protective cover is not reduced, so a decrease in the response of specific gas concentration detection is also further reduced. Here, the phrase "the element-side opening is open in the tip end direction" includes a case the element-side opening is open parallel to the tip end direction of the sensor element and a case where the element-side opening is open at an angle with respect to the tip end direction so as to approach the sensor element from a rear end side of the sensor element toward a tip end side of the sensor element.

In the gas sensor of the present invention, the inner protective cover may have a first member and a second member, and the first member and the second member may form the one or more element chamber inlets as a gap between the first member and the second member. In addition, the first member may have a first cylinder portion surrounding the sensor element, the second member may have a second cylinder portion larger in diameter than the first cylinder portion, and the one or more element chamber inlets may be a cylindrical gap between an outer peripheral surface of the first cylinder portion and an inner peripheral surface of the second cylinder portion.

In the present invention, a protective cover for protecting a sensor element having a gas inlet port that introduces measurement-object gas and capable of detecting a specific gas concentration of the measurement-object gas that has flowed in from the gas inlet port, the protective cover includes:

an inner protective cover having inside a sensor element chamber for disposing a tip end of the sensor element and the gas inlet port inside, and having one or more element chamber inlets that are inlets to the sensor element chamber and one or more element chamber outlets that are outlets from the sensor element chamber; and an outer protective cover disposed outside the inner protective cover and having one or more outer inlets that are inlets for the measurement-object gas from an outside and one or more outer outlets that are outlets for the measurement-object gas to the outside, wherein the outer protective cover and the inner protective cover form, as spaces between the outer protective cover and the inner protective cover, a first gas chamber that is at least part of a flow channel for the measurement-object gas between the one or more outer inlets and the one or more element chamber inlets and a second gas chamber that is at least part of a flow channel for the measurement-object gas between the one or more outer outlets and the one or more element chamber outlets and that does not directly communicate with the first gas chamber, and a total cross-sectional area A [mm$^2$] of the one or more outer inlets, a total cross-sectional area B [mm$^2$] of the one or more element chamber inlets, a total cross-sectional area C [mm$^2$] of the one or more element chamber outlets, and a total cross-sectional area D [mm$^2$] of the one or more outer outlets satisfy B>A>C>D, a cross-sectional area ratio A/D that is a ratio between the total cross-sectional area A and the total cross-sectional area D is greater than a value of 2.0 and less than or equal to a value of 5.0, and A×B×C×D that is a product of the total cross-sectional areas A to D is greater than or equal to a value of 3000 and less than or equal to a value of 8500.

By disposing the tip end of the sensor element and the gas inlet port in the sensor element chamber of the protective cover, advantageous effects of reducing a decrease in response at a low flow speed of measurement-object gas and reducing a decrease in heat retaining property are obtained as in the case of the above-described gas sensor of the present invention. In the protective cover of the present invention, various modes of the above-described gas sensor may be employed.

DETAILED DESCRIPTION OF THE INVENTION

Figure 1:
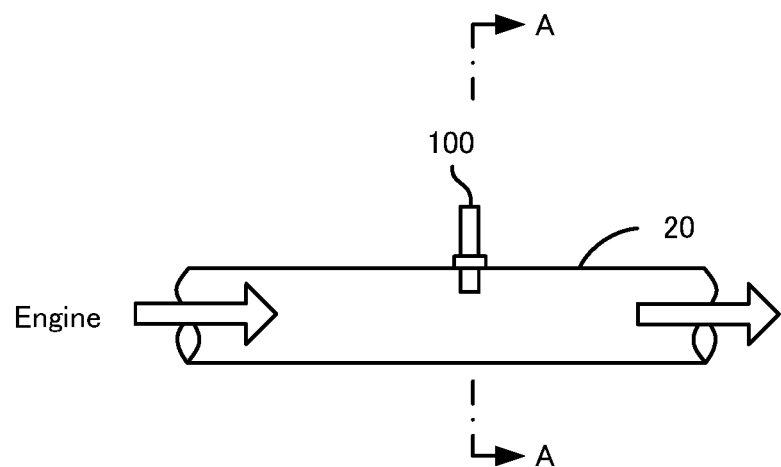
FIG. 1 is a schematic diagram of a state where a gas sensor 100 is attached to a pipe 20.
Figure 2:
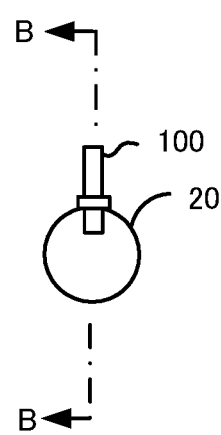
FIG. 2 is a cross-sectional view taken along the line A-A in FIG. 1.
Figure 3:
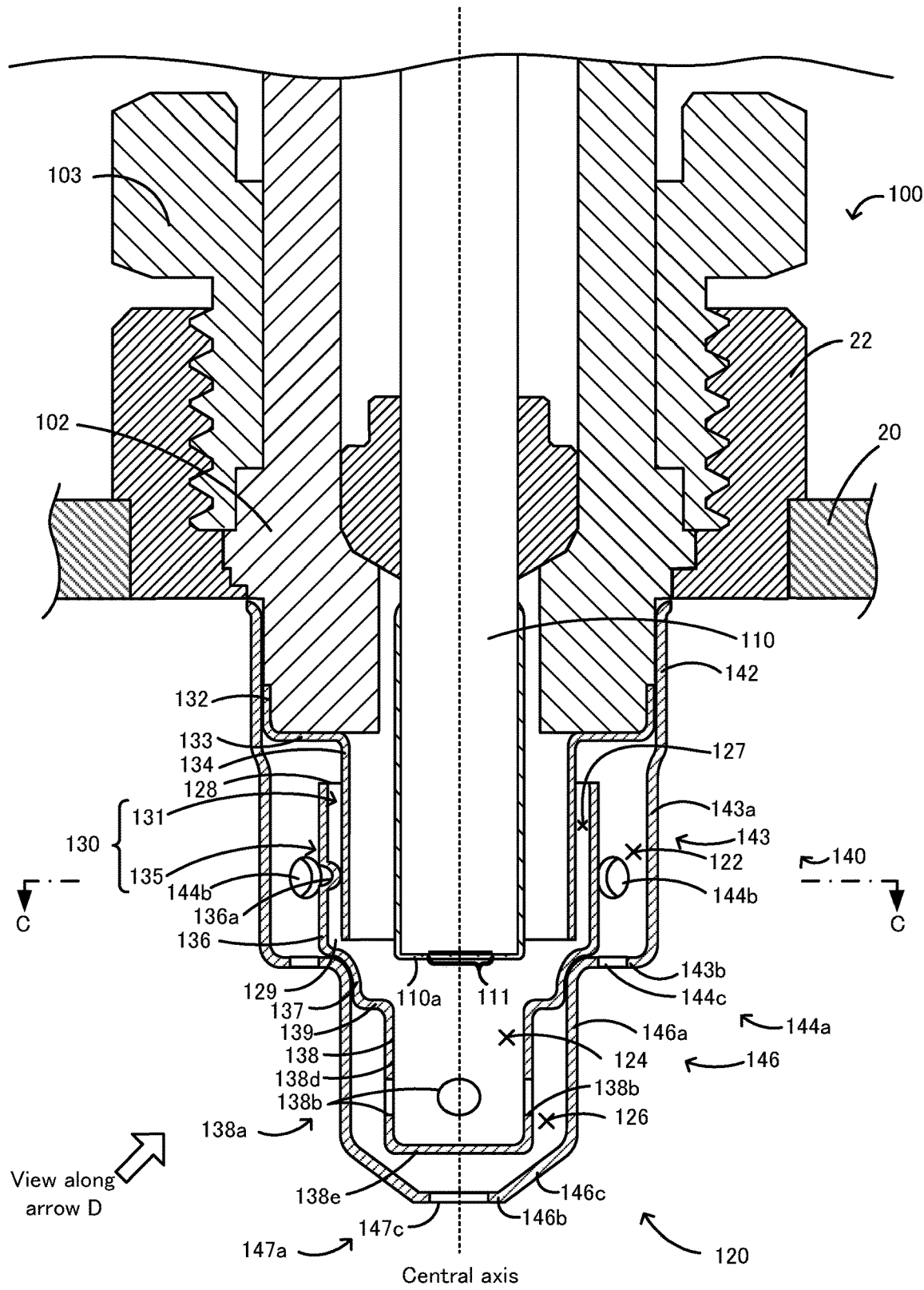
FIG. 3 is a cross-sectional view taken along the line B-B in FIG. 2.
Figure 4:
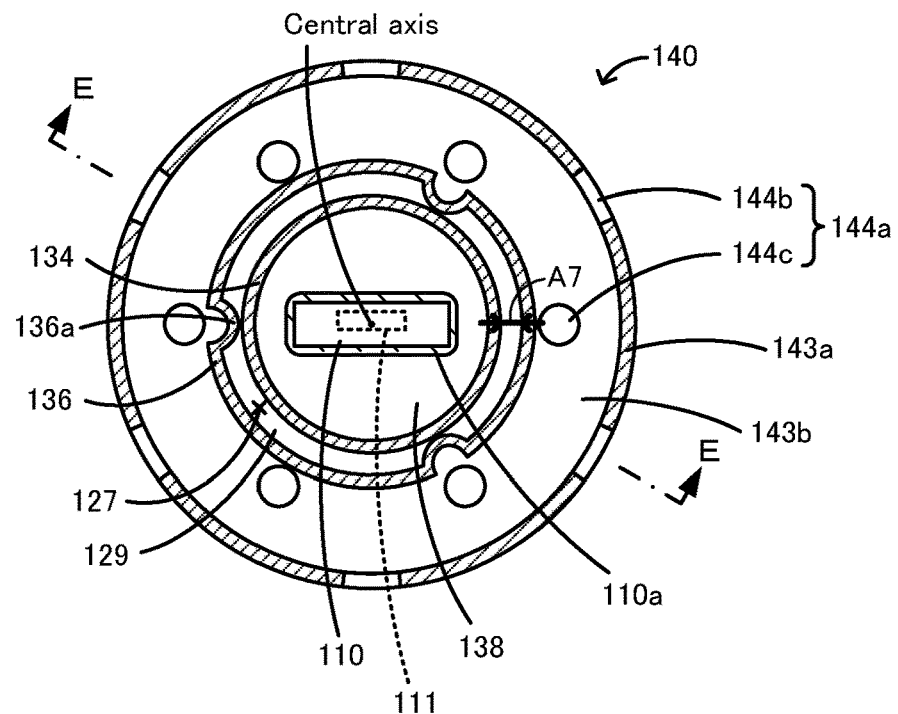
FIG. 4 is a cross-sectional view taken along the line C-C in FIG. 3.
Figure 5:
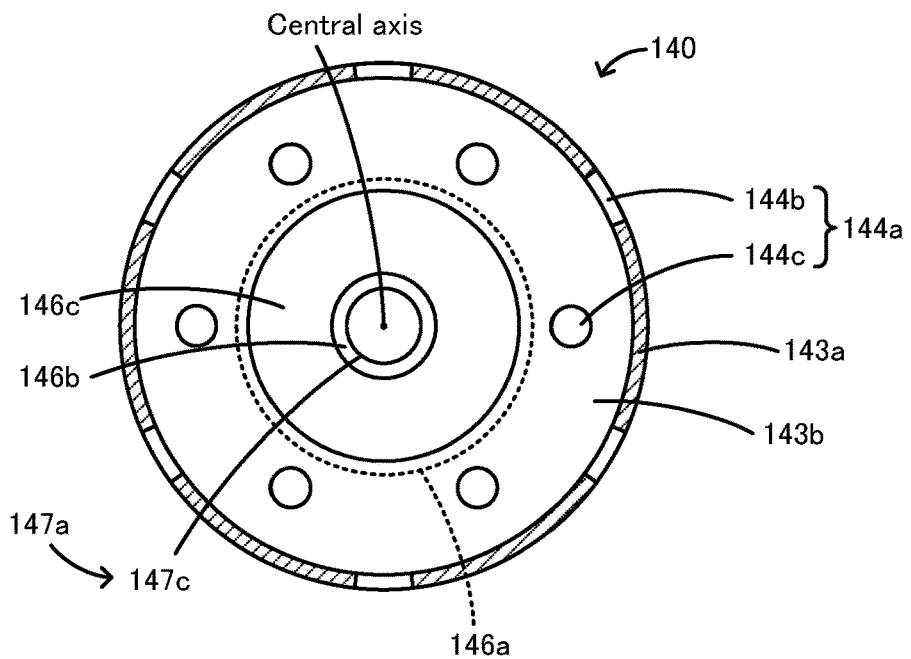
FIG. 5 is a cross-sectional view of an outer protective cover 140, taken along the line C-C in FIG. 3.
Figure 6:
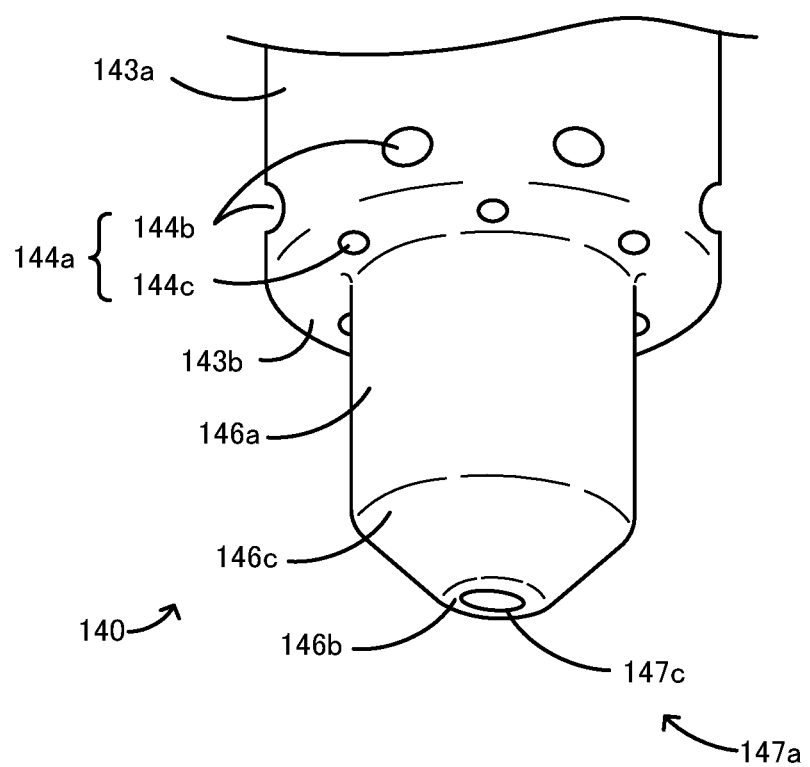
FIG. 6 is a view along the arrow D in FIG. 3.
Figure 7:
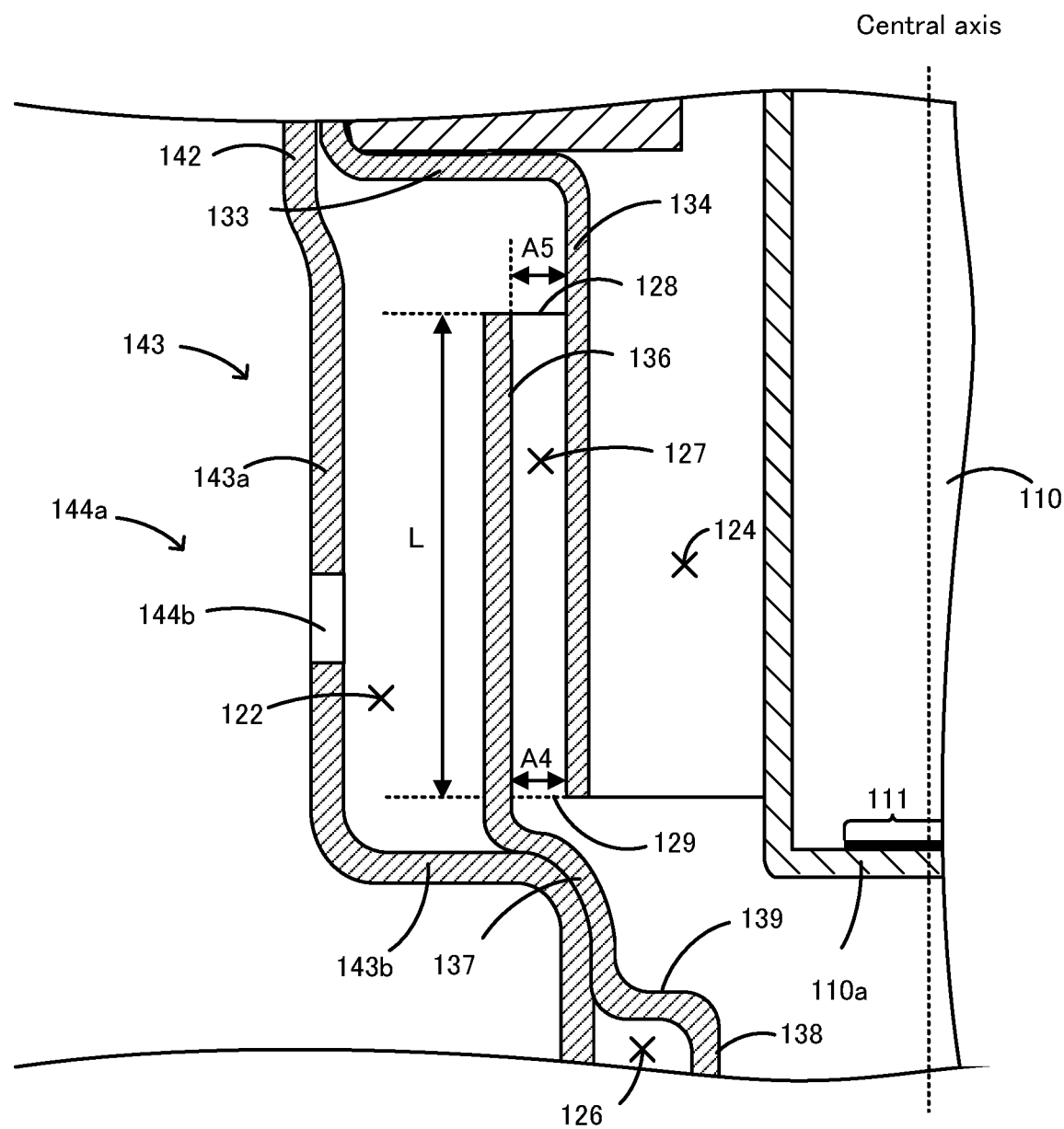
FIG. 7 is a partially enlarged cross-sectional view taken along the line E-E in FIG. 4.

Next, an embodiment of the present invention will be described with reference to the drawings. FIG. 1 is a schematic diagram of a state where a gas sensor 100 is attached to a pipe 20. FIG. 2 is a cross-sectional view taken along the line A-A in FIG. 1. FIG. 3 is a cross-sectional view taken along the line B-B in FIG. 2. FIG. 4 is a cross-sectional view taken along the line C-C in FIG. 3. FIG. 5 is a cross-sectional view of an outer protective cover 140, taken along the line C-C in FIG. 3. FIG. 5 corresponds to a diagram excluding a first cylinder portion 134, a second cylinder portion 136, a tip end portion 138, and a sensor element 110 from FIG. 4. FIG. 6 is a view along the arrow D in FIG. 3. FIG. 7 is a partially enlarged cross-sectional view taken along the line E-E in FIG. 4.

As shown in FIG. 1, the gas sensor 100 is attached inside the pipe 20 that is an exhaust pathway from an engine of a vehicle and is configured to detect a specific gas concentration that is the concentration of at least any one specific gas of gas components, such as NOx, 02, and NH$_3$, contained in exhaust gas as measurement-object gas emitted from the engine. As shown in FIG. 2, the gas sensor 100 is fixed to the pipe 20 in a state where a central axis of the gas sensor 100 is perpendicular to the flow of measurement-object gas in the pipe 20. The gas sensor 100 may be fixed to the pipe 20 in a state where the central axis of the gas sensor 100 is perpendicular to the flow of measurement-object gas in the pipe 20 and inclined at a predetermined angle (for example, 45°) with respect to a vertical direction.

As shown in FIG. 3, the gas sensor 100 includes a sensor element 110 having a function to detect a specific gas concentration in measurement-object gas, and a protective cover 120 that protects the sensor element 110. The gas sensor 100 includes a metal housing 102 and a metal bolt 103 provided with external thread on its outer peripheral surface. The housing 102 is inserted in a fixing member 22 welded to the pipe 20 and provided with internal thread on its inner peripheral surface, and the housing 102 is fixed in the fixing member 22 by further inserting the bolt 103 into the fixing member 22. Thus, the gas sensor 100 is fixed to the pipe 20. A direction in which measurement-object gas flows inside the pipe 20 is a direction from the left toward the right in FIG. 3.

The sensor element 110 is an element having a narrow long planar shape and has such a structure that a plurality of oxygen-ion-conductive solid electrolyte layers made of zirconia (ZrO$_2$) or the like is laminated. The sensor element 110 has a gas inlet port 111 that introduces therein measurement-object gas and is configured to be capable of detecting a specific gas concentration of measurement-object gas having flowed in from the gas inlet port 111. In the present embodiment, the gas inlet port 111 is open at the tip end surface of the sensor element 110 (the lower surface of the sensor element 110 in FIG. 3). The sensor element 110 includes inside a heater that plays a role in temperature adjustment to retain temperature by heating the sensor element 110. The structure of the sensor element 110 and the principle of detecting a specific gas concentration are known and are described in, for example, Japanese Unexamined Patent Application Publication No. 2008-164411. The tip end (the lower end in FIG. 3) and gas inlet port 111 of the sensor element 110 are disposed inside the sensor element chamber 124. A direction (downward direction in FIG. 3) from the rear end of the sensor element 110 toward the tip end of the sensor element 110 is also referred to as tip end direction.

The sensor element 110 includes a porous protective layer 110a that covers at least part of the surface. In the present embodiment, the porous protective layer 110a is formed on five surfaces out of six surfaces of the sensor element 110 and covers almost all the surface exposed to the inside of the sensor element chamber 124. Specifically, the porous protective layer 110a covers the entire tip end surface (lower surface of FIG. 3) at which the gas inlet port 111 is formed in the sensor element 110. The porous protective layer 110a covers a side closer to the tip end surface of the sensor element 110 on the four surfaces (the upper, lower, right, and left surfaces of the sensor element 110 in FIG. 4) connected to the tip end surface of the sensor element 110. The porous protective layer 110a plays a role in, for example, suppressing occurrence of crack in the sensor element 110 as a result of adhesion of moisture or the like in measurement-object gas. The porous protective layer 110a also plays a role in suppressing adhesion of an oil component and the like contained in measurement-object gas to an electrode (not shown) or the like of the surface of the sensor element 110. The porous protective layer 110a is made of, for example, a porous material, such as alumina porous material, zirconia porous material, spinel porous material, cordierite porous material, titania porous material, and magnesia porous material. The porous protective layer 110a may be formed by, for example, plasma spraying, screen printing, dipping, or the like. The porous protective layer 110a also covers the gas inlet port 111; however, since the porous protective layer 110a is a porous material, measurement-object gas is able to flow through the inside of the porous protective layer 110a and reach the gas inlet port 111. The thickness of the porous protective layer 110a is, for example, 100 μm to 700 μm.

The protective cover 120 is disposed so as to surround the sensor element 110. The protective cover 120 has a closed-end cylindrical inner protective cover 130 that covers the tip end of the sensor element 110 and a closed-end cylindrical outer protective cover 140 that covers the inner protective cover 130. A first gas chamber 122 and a second gas chamber 126 are formed as spaces surrounded by the inner protective cover 130 and the outer protective cover 140, and a sensor element chamber 124 is formed as a space surrounded by the inner protective cover 130. The central axes of the gas sensor 100, the sensor element 110, the inner protective cover 130, and the outer protective cover 140 are coaxial with one another. The protective cover 120 is made of metal (for example, stainless steel).

The inner protective cover 130 includes a first member 131 and a second member 135. The first member 131 has a cylindrical large-diameter portion 132, a cylindrical first cylinder portion 134 smaller in diameter than the large-diameter portion 132, and a stepped portion 133 that connects the large-diameter portion 132 and the first cylinder portion 134. The first cylinder portion 134 surrounds the sensor element 110. The second member 135 has a second cylinder portion 136 larger in diameter than the first cylinder portion 134, a closed-end cylindrical tip end portion 138 located on a side in the tip end direction (downward direction in FIG. 3) of the sensor element 110 with respect to the second cylinder portion 136, a stepped portion 139 disposed so as to be connected to the upper end of the tip end portion 138 and protruding outward from the outer peripheral surface of the tip end portion 138, and a connection portion 137 connecting the lower end of the second cylinder portion 136 and the stepped portion 139. The tip end portion 138 has a side portion 138d and a bottom portion 138e. The tip end portion 138 has one or more element chamber outlets 138a that communicate with the sensor element chamber 124 and the second gas chamber 126 and that are outlets for measurement-object gas from the sensor element chamber 124. The element chamber outlets 138a include a plurality of (four in the present embodiment) horizontal holes 138b formed at equal intervals at the side portion 138d. The element chamber outlets 138a are not disposed at the bottom portion 138e of the tip end portion 138. The diameter of each element chamber outlet 138a is, for example, 0.5 mm to 3.0 mm, and it is desirable that the diameter of each element chamber outlet 138a be 1.0 mm to 2.5 mm. In the present embodiment, the diameter of each of the plurality of horizontal holes 138b is set to the same value. The element chamber outlets 138a are formed on a side in the tip end direction (downward direction in FIG. 3) of the sensor element 110 with respect to the gas inlet port 111. In other words, the element chamber outlets 138a are located away (in the downward direction in FIG. 3) from the gas inlet port 111 when viewed from the rear end of the sensor element 110 (the upper end (not shown) of the sensor element 110 in FIG. 3).

The large-diameter portion 132, the first cylinder portion 134, the second cylinder portion 136, and the tip end portion 138 have the same central axis. The inner peripheral surface of the large-diameter portion 132 is in contact with the housing 102. Thus, the first member 131 is fixed to the housing 102. In the second member 135, the outer peripheral surface of the connection portion 137 is in contact with the inner peripheral surface of the outer protective cover 140 and is fixed to the inner peripheral surface of the outer protective cover 140 by welding or the like. The second member 135 may be fixed by forming the outside diameter of the tip end side of the connection portion 137 so as to be slightly larger than the inside diameter of the tip end portion 146 of the outer protective cover 140 and press-fitting the tip end side of the connection portion 137 into the tip end portion 146.

A plurality of protruding portions 136a that protrude toward the outer peripheral surface of the first cylinder portion 134 and that are in contact with the outer peripheral surface are formed on the inner peripheral surface of the second cylinder portion 136. In the present embodiment, as shown in FIG. 4, three protruding portions 136a are provided and are disposed equally on the inner peripheral surface of the second cylinder portion 136 along the circumferential direction. Each protruding portion 136a is formed in a substantially semi-spherical shape. With the thus configured protruding portions 136a, the positional relation between the first cylinder portion 134 and the second cylinder portion 136 is easily fixed by the protruding portions 136a. It is desirable that the protruding portions 136a press the outer peripheral surface of the first cylinder portion 134 radially inward. With this configuration, it is possible to further reliably fix the positional relation between the first cylinder portion 134 and the second cylinder portion 136 with the protruding portions 136a. The number of the protruding portions 136a is not limited to three and may be two or may be more than or equal to four. Because fixing of the first cylinder portion 134 to the second cylinder portion 136 tends to be stable, it is desirable that the number of the protruding portions 136a be more than or equal to three.

The inner protective cover 130 forms an element chamber inlet 127 (see FIG. 3, FIG. 4, and FIG. 7) that is a gap between the first member 131 and the second member 135 and that is an inlet for measurement-object gas into the sensor element chamber 124. More specifically, the element chamber inlet 127 is formed as a cylindrical gap (gas flow channel) between the outer peripheral surface of the first cylinder portion 134 and the inner peripheral surface of the second cylinder portion 136. The element chamber inlet 127 has an outer opening 128 that is an opening adjacent to the first gas chamber 122 that is a space in which the outer inlets 144a are disposed, and an element-side opening 129 that is an opening adjacent to the sensor element chamber 124 that is a space in which the gas inlet port 111 is disposed. The outer opening 128 is formed on the rear end side (upper side in FIG. 3) of the sensor element 110 with respect to the element-side opening 129. Therefore, in the pathway of measurement-object gas from the outer inlets 144a to the gas inlet port 111, the element chamber inlet 127 is a flow channel from the rear end side (upper side in FIG. 3) of the sensor element 110 toward the tip end side (lower side in FIG. 3) of the sensor element 110. The element chamber inlet 127 is a flow channel parallel to a rear end-tip end direction (a flow channel in the up-down direction in FIG. 3) of the sensor element 110.

The element-side opening 129 is open in a direction from the rear end of the sensor element 110 toward the tip end of the sensor element 110 and is open parallel to the rear end-tip end direction of the sensor element 110. In other words, the element-side opening 129 is open in the downward direction in FIG. 3 and FIG. 7 (just downward). Therefore, the sensor element 110 is disposed at a position other than a region that is an imaginary extension of the element chamber inlet 127 from the element-side opening 129 (a region just below the element-side opening 129 in FIG. 3 and FIG. 7). Thus, it is possible to reduce a situation in which measurement-object gas flowing out from the element-side opening 129 directly strikes the surface of the sensor element 110, so it is possible to suppress a decrease in the heat retaining property of the sensor element 110.

The outer peripheral surface of the first cylinder portion 134 and the inner peripheral surface of the second cylinder portion 136 are spaced apart by a distance A4 (see FIG. 7) in the radial direction of the cylinder at the element-side opening 129 and are spaced apart by a distance A5 in the radial direction of the cylinder at the outer opening 128. The outer peripheral surface of the first cylinder portion 134 and the inner peripheral surface of the second cylinder portion 136 are spaced apart by a distance A7 in a part (the cross section shown in FIG. 4) where the protruding portions 136a and the first cylinder portion 134 contact with each other. The distance A4, the distance A5, and the distance A7 each are, for example, 0.3 mm to 2.4 mm. By adjusting the values of the distance A4 and the distance A5, it is possible to adjust the opening area of the element-side opening 129 and the opening area of the outer opening 128. In the present embodiment, it is assumed that the distance A4, the distance A5, and the distance A7 are equal to one another and the opening area of the element-side opening 129 and the opening area of the outer opening 128 are equal to each other. In the present embodiment, the distance A4 (the distance A5, or the distance A7) is equal to a value of half of the difference between the outside diameter of the first cylinder portion 134 and the inside diameter of the second cylinder portion 136. A distance in the up-down direction between the element-side opening 129 and the outer opening 128, that is, a distance L of the element chamber inlet 127 in the up-down direction (which corresponds to the pathway length of the element chamber inlet 127) is, for example, greater than 0 mm and less than or equal to 6.6 mm. The distance L may be greater than or equal to 3 mm or may be less than or equal to 5 mm.

As shown in FIG. 3, the outer protective cover 140 has a cylindrical large-diameter portion 142, a cylindrical body portion 143 connected to the large-diameter portion 142 and smaller in diameter than the large-diameter portion 142, and a closed-end cylindrical tip end portion 146 smaller in inside diameter than the body portion 143. The body portion 143 has a side portion 143a having a side surface along a central axis direction (up-down direction in FIG. 3) of the outer protective cover 140, and a stepped portion 143b that is a bottom portion of the body portion 143 and that connects the side portion 143a and the tip end portion 146. The central axes of the large-diameter portion 142, the body portion 143, and the tip end portion 146 all are the same as the central axis of the inner protective cover 130. The large-diameter portion 142 is in contact with the housing 102 and the large-diameter portion 132 on its inner peripheral surface. Thus, the outer protective cover 140 is fixed to the housing 102. The body portion 143 is located so as to cover the outer circumference of the first cylinder portion 134 and the second cylinder portion 136. The large-diameter portion 142 and the body portion 143 may have diameters equal to each other. The tip end portion 146 is located so as to cover the tip end portion 138, and the inner peripheral surface is in contact with the outer peripheral surface of the connection portion 137. The tip end portion 146 has a side portion 146a having a side surface along the central axis direction (up-down direction in FIG. 3) of the outer protective cover 140 and of which the outside diameter is smaller than the inside diameter of the side portion 143a, a bottom portion 146b that is the bottom portion of the outer protective cover 140, and a tapered portion 146c that connects the side portion 146a and the bottom portion 146b and that reduces in diameter from the side portion 146a toward the bottom portion 146b. The tip end portion 146 is located on the side in the tip end direction with respect to the body portion 143. The outer protective cover 140 has one or more (in the present embodiment, multiple and, specifically, 12) outer inlets 144a that are formed in the body portion 143 and that are inlets for measurement-object gas from the outside, and one or more outer outlets 147a (in the present embodiment, one) that are formed in the tip end portion 146 and that are outlets for measurement-object gas to the outside.

The outer inlets 144a are holes that communicate with the outer side (outside) of the outer protective cover 140 and the first gas chamber 122. The outer inlets 144a include one or more (in the present embodiment, multiple and, specifically, six) horizontal holes 144b formed at equal intervals in the side portion 143a, and one or more (in the present embodiment, multiple and, specifically, six) vertical holes 144c formed at equal intervals in the stepped portion 143b (see FIG. 3 to FIG. 6). The outer inlets 144a (horizontal holes 144b and vertical holes 144c) are holes perforated in a circular shape. The diameter of each of the 12 outer inlets 144a is, for example, 0.5 mm to 2 mm. The diameter of each outer inlet 144a may be less than or equal to 1.5 mm. In the present embodiment, the diameter of each of the plurality of horizontal holes 144b is the same value, and the diameter of each of the plurality of vertical holes 144c is the same value. The diameter of each horizontal hole 144b is greater than the diameter of each vertical hole 144c. As shown in FIG. 4 and FIG. 5, the outer inlets 144a are formed such that the horizontal holes 144b and the vertical holes 144c are alternately located at equal intervals along the circumferential direction of the outer protective cover 140. In other words, an angle formed between a line connecting the center of each horizontal hole 144b and the central axis of the outer protective cover 140 and a line connecting the center of the vertical hole 144c adjacent to that horizontal hole 144b and the central axis of the outer protective cover 140 in FIG. 4 and FIG. 5 is 30° (360°/12).

The outer outlet 147a is a hole that communicates with the outer side (outside) of the outer protective cover 140 and the second gas chamber 126. The outer outlet 147a is configured as one vertical hole 147c formed at the center of the bottom portion 146b of the tip end portion 146 (see FIG. 3, FIG. 5, and FIG. 6). Different from the outer inlets 144a, the outer outlet 147a is not disposed at the side portion of the outer protective cover 140 (here, the side portion 146a of the tip end portion 146). The outer outlet 147a (here, the vertical hole 147c) is a hole perforated in a circular shape. The diameter of the outer outlet 147a is, for example, 0.5 mm to 3.6 mm. The diameter of the outer outlet 147a may be 1.4 mm to 2.5 mm. In the present embodiment, the diameter of the vertical hole 147c is set to a value greater than the diameter of the horizontal hole 144b or the vertical hole 144c.

The outer protective cover 140 and the inner protective cover 130 form the first gas chamber 122 as a space between the body portion 143 and the inner protective cover 130. More specifically, the first gas chamber 122 is a space surrounded by the stepped portion 133, the first cylinder portion 134, the second cylinder portion 136, the large-diameter portion 142, the side portion 143a, and the stepped portion 143b. The sensor element chamber 124 is formed as a space surrounded by the inner protective cover 130. The outer protective cover 140 and the inner protective cover 130 form the second gas chamber 126 as a space between the tip end portion 146 and the inner protective cover 130. More specifically, the second gas chamber 126 is a space surrounded by the tip end portion 138 and the tip end portion 146. Since the inner peripheral surface of the tip end portion 146 is in contact with the outer peripheral surface of the connection portion 137, the first gas chamber 122 and the second gas chamber 126 do not directly communicate with each other.

Here, the flow of measurement-object gas inside the protective cover 120 at the time when the gas sensor 100 detects a specific gas concentration will be described. Measurement-object gas that flows in the pipe 20 initially passes through at least any one of the plurality of outer inlets 144a (the horizontal holes 144b and the vertical holes 144c) and flows into the first gas chamber 122. Subsequently, measurement-object gas flows from the first gas chamber 122 into the element chamber inlet 127 via the outer opening 128, passes through the element chamber inlet 127, flows out from the element-side opening 129, and flows into the sensor element chamber 124. Measurement-object gas having flowed from the element-side opening 129 into the sensor element chamber 124 at least partially reaches the gas inlet port 111 of the sensor element 110. When measurement-object gas reaches the gas inlet port 111 and flows into the inside of the sensor element 110, the sensor element 110 generates an electrical signal (voltage or current) according to a specific gas concentration in the measurement-object gas, and the specific gas concentration is detected based on the electrical signal. Measurement-object gas in the sensor element chamber 124 flows into the second gas chamber 126 through at least any one of the element chamber outlets 138a (the horizontal holes 138b) and flows out from there to the outside through the outer outlet 147a. The output of a heater inside the sensor element 110 is controlled by a controller (not shown) such that the sensor element 110 is maintained at a predetermined temperature.

In the outer protective cover 140, a cross-sectional area ratio A/D that is a ratio between a total cross-sectional area A [mm$^2$] of the outer inlets 144a and a total cross-sectional area D [mm$^2$] of the outer outlet 147a is greater than a value of 2.0 and less than or equal to a value of 5.0. When the cross-sectional area ratio A/D is greater than a value of 2.0, the flow rate of measurement-object gas flowing in from the outer inlets 144a tends to increase since the total cross-sectional area A is relatively large, and the flow of measurement-object gas that attempts to flow in (flow backward) from the outer outlet 147a tends to decrease since the total cross-sectional area D is relatively small. With this configuration, a space around the gas inlet port 111 is easily replaced by measurement-object gas having flowed in. Therefore, the response of specific gas concentration detection improves. When the total cross-sectional area D is too small, the flow rate of measurement-object gas that flows out from the outer outlet 147a may decrease and, as a result, the response may decrease; however, when the cross-sectional area ratio A/D is less than or equal to a value of 5.0, such a decrease in response is reduced. Adjustment of the cross-sectional area ratio A/D may be performed by, for example, adjusting the number of the outer inlets 144a and the number of the outer outlets 147a or adjusting the cross-sectional area of each outer inlet 144a and the cross-sectional area of each outer outlet 147a.

The inner protective cover 130 is formed such that a total cross-sectional area B [mm$^2$] of the element chamber inlet 127 is greater than a total cross-sectional area C [mm$^2$] of the element chamber outlets 138a. The outer protective cover 140 and the inner protective cover 130 are configured such that the total cross-sectional areas A to D satisfy B>A>C>D and A×B×C×D is greater than or equal to a value of 3000 and less than or equal to a value of 8500. With the thus configured gas sensor 100, in the case where the flow speed of measurement-object gas is low, flow of measurement-object gas is smooth, most of measurement-object gas that flows in from the outer inlets 144a flows into the sensor element chamber 124, and most of measurement-object gas having flowed into the sensor element chamber 124 flows out from the outer outlet 147a without flowing backward. In other words, when the total cross-sectional area B is greater than the total cross-sectional area A, most of gas having flowed in from the outer inlets 144a flows into the sensor element chamber 124 through the element chamber inlet 127, so the flow rate of measurement-object gas that flows into the sensor element chamber 124 tends to increase. When the total cross-sectional area A is greater than the total cross-sectional area C, the flow rate of measurement-object gas that attempts to flow in (flow backward) from the element chamber outlets 138a tends to decrease. In addition, when the total cross-sectional area C is greater than the total cross-sectional area D, the flow rate of measurement-object gas that attempts to flow in (flow backward) from the outer outlet 147a tends to decrease. With this configuration, even when the flow speed of measurement-object gas is low, a space around the gas inlet port 111 is easily replaced by measurement-object gas having flowed in. Therefore, even when the flow speed of measurement-object gas is low, it is possible to improve the response of specific gas concentration detection without increasing the total cross-sectional areas A to D of the outlets and inlets to such an extent that the heat retaining property decreases.

In the present embodiment, the total cross-sectional area A is the sum of the total cross-sectional area of the six horizontal holes 144*b* and the total cross-sectional area of the six vertical holes 144*c*. The total cross-sectional area C is the total cross-sectional area of the four horizontal holes 138*b*. The total cross-sectional area D is the cross-sectional area of the one vertical hole 147*c*. It is assumed that the cross-sectional area of each outer inlet 144*a* is an area in a direction perpendicular to the direction of measurement-object gas that passes through the outer inlet 144*a*. In the present embodiment, each of the outer inlets 144*a* is a circular hole, so the area of the circle is a cross-sectional area. This also similarly applies to the element chamber outlets 138*a* and the outer outlet 147*a*. When, in one of the outer inlets 144*a*, the cross-sectional area of the outer inlet 144*a* is not constant, that is, in, for example, the case where the cross-sectional area at the inlet side (the outer surface side of the outer protective cover 140) and the cross-sectional area at the outlet side (the inner surface side of the outer protective cover 140) are different or other cases, the minimum value of the cross-sectional area is used as the cross-sectional area of that outer inlet 144*a*. This also similarly applies to the element chamber outlets 138*a* and the outer outlet 147*a*. In the present embodiment, the total cross-sectional area B is the cross-sectional area of the element chamber inlet 127 and is the cross-sectional area of a cylindrical gap between the outer peripheral surface of the first cylinder portion 134 and the inner peripheral surface of the second cylinder portion 136. It is assumed that the cross-sectional area of the element chamber inlet 127 is an area in a direction perpendicular to the direction of measurement-object gas that passes through the element chamber inlet 127. In the present embodiment, since the outer peripheral surface of the first cylinder portion 134 and the inner peripheral surface of the second cylinder portion 136 each have a circular shape, the cross-sectional area of the element chamber inlet 127 is a value obtained by subtracting the cross-sectional area of a circle having the outside diameter of the first cylinder portion 134 as a diameter from the cross-sectional area of a circle having the inside diameter of the second cylinder portion 136 as a diameter. When, in the element chamber inlet 127, the cross-sectional area in a direction perpendicular to the direction of flow of measurement-object gas is not constant in the element chamber inlet 127, that is, in, for example, the case where the cross-sectional area of the outer opening 128 and the cross-sectional area of the element-side opening 129 are different from each other or other cases, the minimum value of the cross-sectional area is used as the cross-sectional area of the element chamber inlet 127. In the present embodiment, since the cross-sectional area of the element chamber inlet 127 in a cross section in which the protruding portions 136*a* protrude the most in the element chamber inlet 127, that is, the cross section of FIG. 4, is the minimum value, the cross-sectional area of the element chamber inlet 127 in the cross section of FIG. 4 is the total cross-sectional area B.

With the gas sensor 100 of the present embodiment described in detail above, the cross-sectional area ratio A/D is greater than a value of 2.0 and less than or equal to a value of 5.0, B>A>C>D is satisfied, and A×B×C×D that is the product of the total cross-sectional areas A to D is greater than or equal to a value of 3000 and less than or equal to a value of 8500, so it is possible to reduce a decrease in the response of specific gas concentration detection even when the flow speed of measurement-object gas is low and to reduce a decrease in heat retaining property. It is desirable that the cross-sectional area ratio A/D be greater than or equal to a value of 2.5, it is more desirable that the cross-sectional area ratio A/D be greater than or equal to a value of 3.0, and it is further more desirable that the cross-sectional area ratio A/D be greater than or equal to a value of 3.4. As the cross-sectional area ratio A/D increases, the response of specific gas concentration detection tends to improve. The total cross-sectional area A may be greater than or equal to 10 $mm^2$ and less than or equal to 30 $mm^2$ or may be greater than or equal to 10 $mm^2$ and less than or equal to 18 $mm^2$. The total cross-sectional area B may be greater than or equal to 15 $mm^2$ and less than or equal to 50 $mm^2$ or may be greater than or equal to 15 $mm^2$ and less than or equal to 35 $mm^2$ or may be greater than or equal to 20 $mm^2$ and less than or equal to 35 $mm^2$. The total cross-sectional area C may be greater than or equal to 5 $mm^2$ and less than or equal to 15 $mm^2$ or may be greater than or equal to 5 $mm^2$ and less than or equal to 10 $mm^2$. The total cross-sectional area D may be greater than or equal to 1.6 $mm^2$ and less than or equal to 10 $mm^2$ or may be greater than or equal to 2.8 $mm^2$ and less than or equal to 3.5 $mm^2$. In addition, a cross-sectional area ratio B/A that is a ratio between the total cross-sectional area B and the total cross-sectional area A may be greater than a value of 1 (that is, B>A) and less than or equal to a value of 4.5 or may be greater than or equal to a value of 1.4 and less than or equal to a value of 3.3. A cross-sectional area ratio A/C that is a ratio between the total cross-sectional area A and the total cross-sectional area C may be greater than a value of 1 (that is, A>C) and less than or equal to a value of 6.0 or may be greater than or equal to a value of 1.1 and less than or equal to a value of 3.0. A cross-sectional area ratio C/D that is a ratio between the total cross-sectional area C and the total cross-sectional area D may be greater than a value of 1 (that is, C>D) and less than or equal to a value of 9.4 or may be greater than or equal to a value of 1.3 and less than or equal to a value of 4.0.

In the gas sensor 100, the outer protective cover 140 has the closed-end cylindrical tip end portion 146 having the side portion 146*a* and the bottom portion 146*b*, and the outer outlet 147*a* is not disposed at the side portion 146*a* of the outer protective cover 140. When the outer outlet 147*a* disposed at the side portion 146*a* of the outer protective cover 140 is present, the response may change depending on the positional relation between the outer outlet 147*a* of the side portion 146*a* and the flow direction of surrounding measurement-object gas. When a change in response due to such a positional relation between the outer outlet 147*a* (here, the horizontal hole) of the side portion 146*a* and the flow direction of surrounding measurement-object gas is large, the response may decrease depending on an orientation in which the gas sensor 100 is attached (an angle in the rotation direction about the central axis of the outer protective cover 140) (see the above-described PTL 2). In contrast, in the gas sensor 100 of the present embodiment, since the outer outlet 147*a* is not disposed at the side portion 146*a*, it is possible to reduce the influence on the response due to an orientation in which the gas sensor 100 is attached. Such an influence on the response due to an orientation in which the gas sensor 100 is attached is referred to as angle dependence.

In the gas sensor 100 of the present embodiment, the outer outlet 147a is not disposed at the side portion 146a, so it is possible to reduce angle dependence. In the outer protective cover 140, the outer outlet 147a is configured as one vertical hole 147c formed at the bottom portion 146b, and the diameter of the vertical hole 147c is relatively large and is greater than, for example, the diameter of the horizontal hole 144b or the vertical hole 144c. Therefore, even when the total cross-sectional area D is set such that B>A>C>D is satisfied, soot is difficult to clog the outer outlet 147a.

In addition, in the gas sensor 100, the inner protective cover 130 has a closed-end cylindrical shape and has the side portion 138d and the bottom portion 138e, and the element chamber outlets 138a are not disposed at the bottom portion 138e of the inner protective cover 130. Generally, the side portion 138d often has a greater area than the bottom portion 138e, and the total cross-sectional area C of the element chamber outlets 138a is easily increased in that case, so C>D is easily achieved. The sensor element 110 is less likely to be exposed to water when the sensor element 110 is not disposed along a line extended from each of the element chamber outlets 138a, and a configuration in which the sensor element is not disposed along a line extended from each element chamber outlet is easily realized when the element chamber outlets 138a are disposed at the side portion 138d of the inner protective cover 130. When the element chamber outlet 138a is disposed at the bottom portion 138e of the inner protective cover 130, the outer outlet 147a disposed at the bottom portion 146b of the outer protective cover 140, the element chamber outlet 138a disposed at the bottom portion 138e of the inner protective cover 130, and the sensor element 110 may be disposed in a line. When the outer outlet 147a, the element chamber outlet 138a, and the sensor element 110 are disposed in a line, there are concerns that the sensor element 110 becomes easy to get wet by water having entered from the outer outlet 147a. In contrast, with the gas sensor 100 of the present embodiment, the element chamber outlets 138a are not disposed at the bottom portion 138e of the inner protective cover 130, so the sensor element 110 is less likely to get wet by water having entered from the outer outlet 147a.

Furthermore, in the gas sensor 100, the inner protective cover 130 forms the element chamber inlet 127 such that the element-side opening 129 is open in the tip end direction. Therefore, it is possible to reduce a situation in which measurement-object gas having flowed out from the element-side opening 129 perpendicularly strikes the surface (surface other than the gas inlet port 111) of the sensor element 110 and to reduce a situation in which measurement-object gas passes along the surface of the sensor element 110 over a long distance and then reaches the gas inlet port 111. Thus, it is possible to further suppress a decrease in the heat retaining property of the sensor element 110. In addition, a decrease in the heat retaining property of the sensor element 110 is suppressed by adjusting the orientation of the opening of the element-side opening 129, and the flow rate or flow speed of measurement-object gas inside the inner protective cover 130 is not reduced, so a decrease in the response of specific gas concentration detection is also further reduced.

The present invention is not limited to the above-described embodiments, and can be carried out by various modes as long as they belong to the technical scope of the invention.

Figure 8:
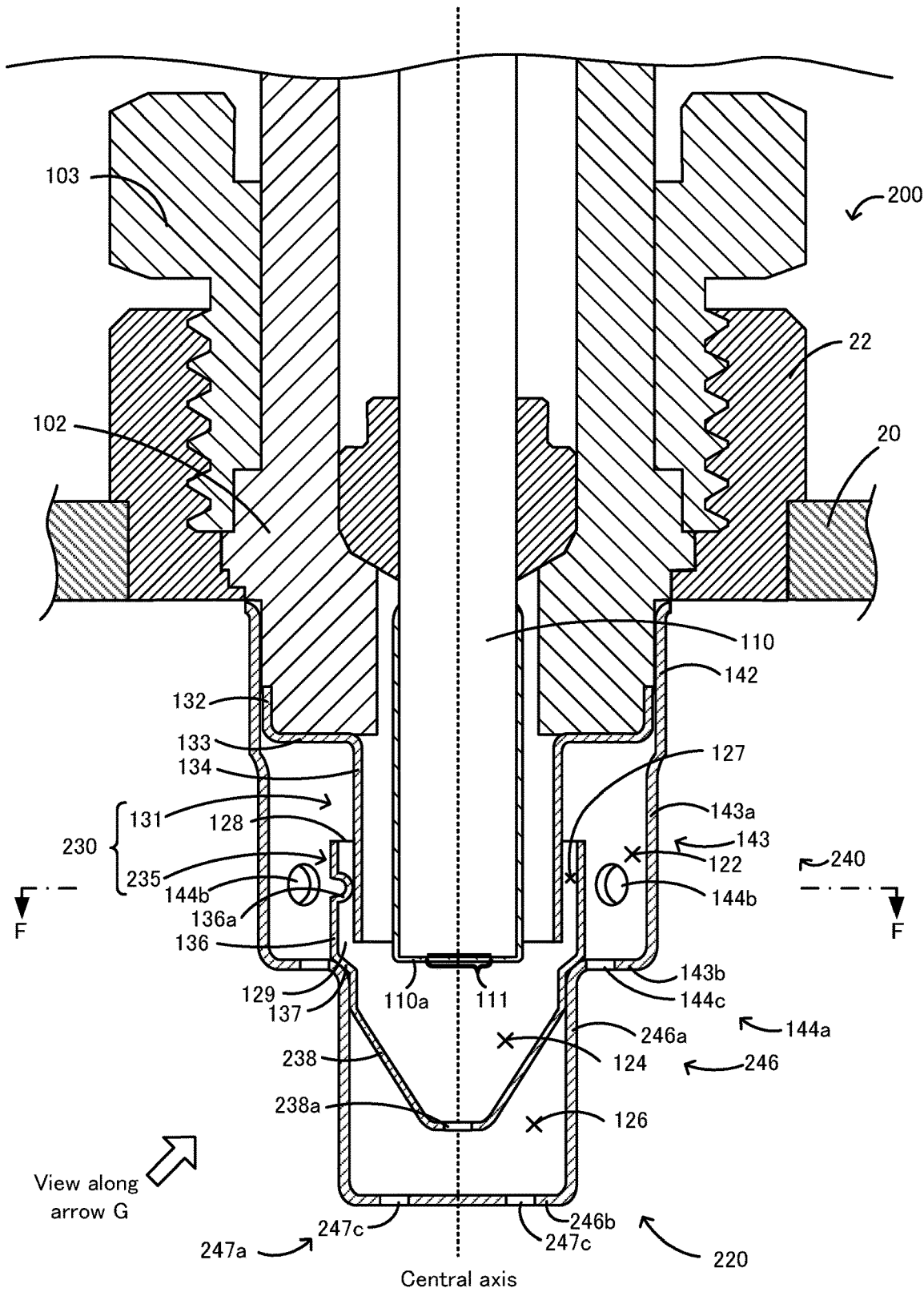
FIG. 8 is a longitudinal sectional view of a gas sensor 200 of a modification.
Figure 9:
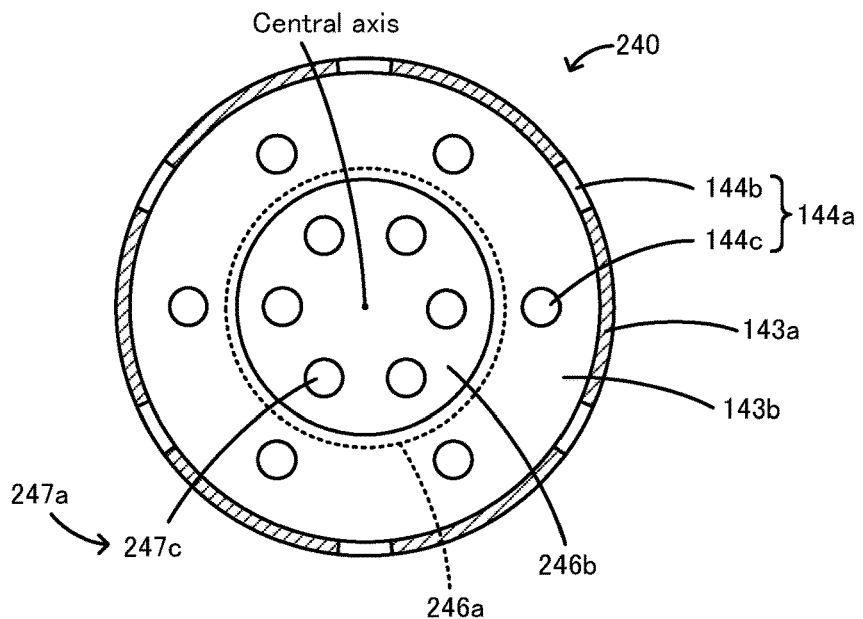
FIG. 9 is a cross-sectional view of an outer protective cover 240, taken along the line F-F in FIG. 8.
Figure 10:
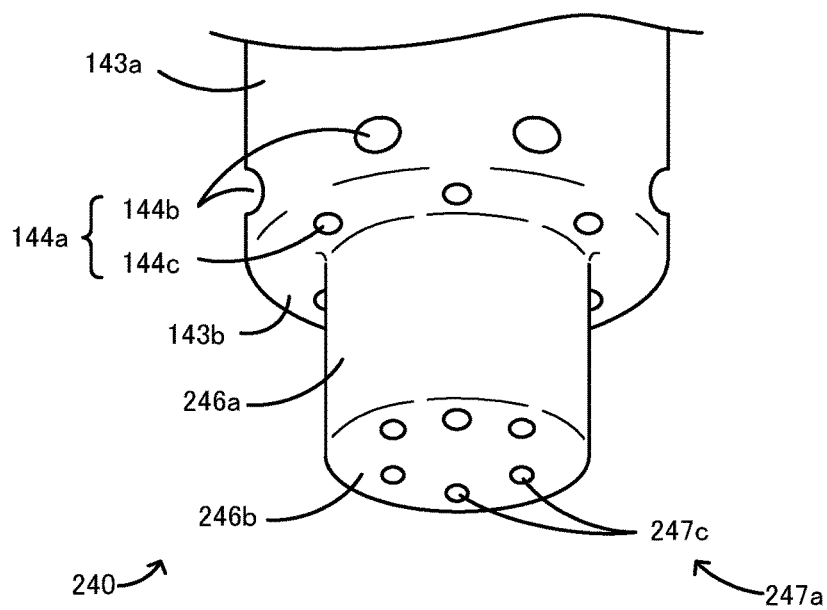
FIG. 10 is a view along the arrow G in FIG. 8.

For example, the shape of the protective cover 120 is not limited to the above-described embodiment. The shape of the protective cover 120 or the shape, number, arrangement, and the like of each of the element chamber inlet 127, element chamber outlet 138a, outer inlet 144a, and outer outlet 147a may be changed as needed. For example, the tip end portion 146 of the outer protective cover 140 has a closed-end cylindrical shape and has the side portion 146a, the bottom portion 146b, and the tapered portion 146c. Alternatively, the tip end portion 146 may have a cylindrical shape without the tapered portion 146c. The tip end portion 138 of the inner protective cover 130 has such a shape that the outside diameter of the side portion 138d is constant and the side portion 138d and the bottom portion 138e have the same diameters. Alternatively, the tip end portion 138 may have such a shape that the outside diameter of the side portion 138d tends to reduce as it approaches the bottom portion 138e, for example, an inverted truncated cone shape. FIG. 8 is a longitudinal sectional view of a gas sensor 200 (which corresponds to the cross-sectional view of the gas sensor 100, taken along the line B-B), in which the tip end portion 146 of the outer protective cover 140 has a cylindrical shape without the tapered portion 146c and the tip end portion 138 of the inner protective cover 130 has an inverted truncated cone shape. FIG. 9 is a cross-sectional view of an outer protective cover 240, taken along the line F-F in FIG. 8. FIG. 10 is a view along the arrow G in FIG. 8. In FIG. 8 to FIG. 10, like reference signs are assigned to the same components as those of the gas sensor 100, and the detailed description thereof is omitted. As shown in FIG. 8, a protective cover 220 of the gas sensor 200 includes an inner protective cover 230 instead of the inner protective cover 130, and includes an outer protective cover 240 instead of the outer protective cover 140. A second member 235 of the inner protective cover 230 has a tip end portion 238 having an inverted truncated cone shape, instead of the tip end portion 138 and the stepped portion 139. The tip end portion 238 has an element chamber outlet 238a that communicates with the sensor element chamber 124 and the second gas chamber 126 and that is an outlet for measurement-object gas from the sensor element chamber 124. The element chamber outlet 238a is a single circular vertical hole formed at the center of the bottom surface of the tip end portion 238. The outer protective cover 240 has a closed-end cylindrical (cylindrical) tip end portion 246 smaller in inside diameter than the body portion 143, instead of the tip end portion 146. The tip end portion 246 has a side portion 246a having a side surface along the central axis direction (up-down direction in FIG. 8) of the outer protective cover 240 and of which the outside diameter is smaller than the inside diameter of the side portion 143a, and a bottom portion 246b that is the bottom portion of the outer protective cover 240. A plurality of (here, six) outer outlets 247a that are outlets for measurement-object gas to the outside is formed at the tip end portion 246. The outer outlets 247a include a plurality of (here, six) vertical holes 247c formed at equal intervals along the circumferential direction of the outer protective cover 240 at the bottom portion 246b of the tip end portion 246 (see FIG. 8 to FIG. 10). With the thus configured gas sensor 200 as well, when the cross-sectional area ratio A/D is greater than a value of 2.0 and less than or equal to a value of 5.0, B>A>C>D is satisfied, and A×B×C×D is greater than or equal to a value of 3000 and less than or equal to a value of 8500, similar advantageous effects to those of the above-described embodiment are obtained.

In the above-described embodiment, the element chamber inlet 127 is a gap between the first member 131 and the second member 135; however, the configuration is not limited thereto. The element chamber inlet may have any shape as long as the element chamber inlet is an inlet to the sensor element chamber 124. For example, the element chamber inlet may be a through-hole formed in the inner protective cover 130. When the element chamber inlet is a through-hole as well, the element chamber inlet may form a flow channel from the rear end side of the sensor element 110 toward the tip end side of the sensor element 110. For example, the element chamber inlet may be a vertical hole or a hole inclined at an angle with respect to the up-down direction of FIG. 3. The element-side opening 129 may be open in the tip end direction. The number of the element chamber inlets 127 is not limited to one and may be multiple. The element chamber outlets 138a, the outer inlets 144a, and the outer outlet 147a each are also not limited to a hole and may be a gap between a plurality of members that make up the protective cover 120, and it is sufficient that the number of each is one or more. The outer inlets 144a include the horizontal holes 144b and the vertical holes 144c. Alternatively, the outer inlets 144a may include only any one-type hole. In addition to or instead of the horizontal holes 144b and the vertical holes 144c, an corner hole may be formed at an corner portion at the boundary between the side portion 143a and the stepped portion 143b. For the element chamber inlet 127, the element chamber outlets 138a, and the outer outlet 147a as well, similarly, any one or more types of a horizontal hole, a vertical hole, and an corner hole may be formed. The outer outlets 147a may include a through-hole provided at the tapered portion 146c. As described above, it is desirable that the outer outlets 147a include no horizontal hole, that is, it is desirable that no outer outlet 147a be disposed at the side portion 146a. As described above, it is desirable that the element chamber outlets 138a include no vertical hole, that is, it is desirable that no element chamber outlet 138a be disposed at the bottom portion 138e.

In the above-described embodiment, the protruding portions 136a are formed on the inner peripheral surface of the second cylinder portion 136; however, the configuration is not limited thereto. It is sufficient that a protruding portion is formed on at least one of the outer peripheral surface of the first cylinder portion 134 and the inner peripheral surface of the second cylinder portion 136 so as to protrude toward the other surface and contact with the other surface. In the above-described embodiment, as shown in FIG. 3 and FIG. 4, the outer peripheral surfaces of portions where the protruding portions 136a are formed in the second cylinder portion 136 are recessed inward; however, the configuration is not limited thereto. Alternatively, the outer peripheral surfaces do not need to be recessed. The protruding portions 136a are not limited to a semi-spherical shape and may be any shape. The protruding portions 136a do not need to be formed on the outer peripheral surface of the first cylinder portion 134 or on the inner peripheral surface of the second cylinder portion 136.

Figure 11:
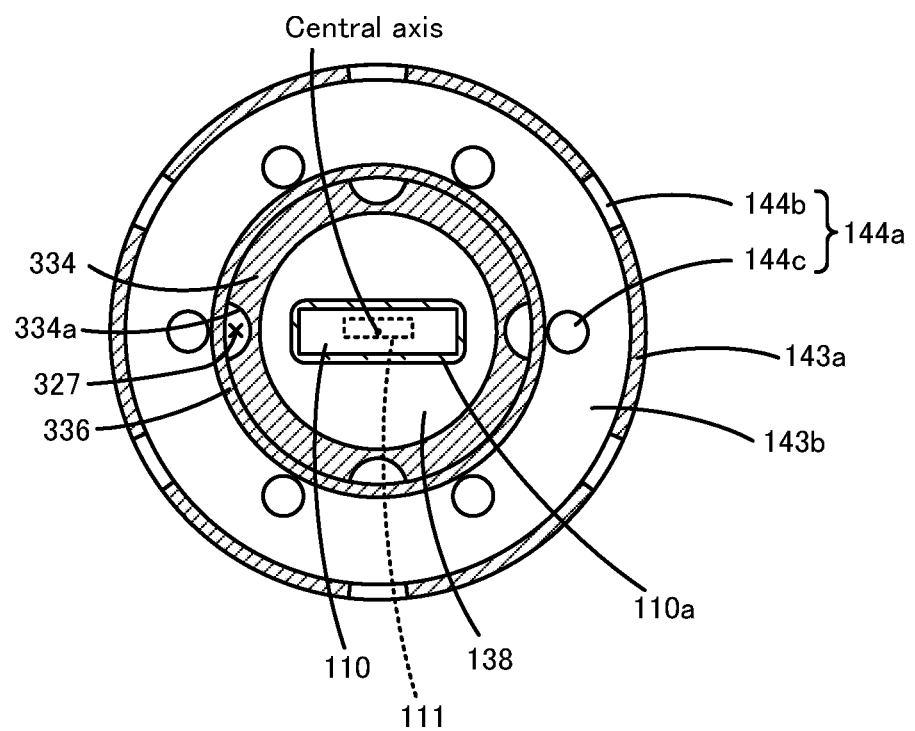
FIG. 11 is a cross-sectional view showing element chamber inlets 327 of a modification.

In the above-described embodiment, the element chamber inlet 127 is a cylindrical gap between the outer peripheral surface of the first cylinder portion 134 and the inner peripheral surface of the second cylinder portion 136; however, the configuration is not limited thereto. For example, a recessed portion (groove) may be formed on at least one of the outer peripheral surface of the first cylinder portion and the inner peripheral surface of the second cylinder portion, and the element chamber inlet may be a gap formed by the recessed portion between the first cylinder portion and the second cylinder portion. FIG. 11 is a cross-sectional view showing an element chamber inlet 327 of a modification. As shown in FIG. 11, the outer peripheral surface of the first cylinder portion 334 and the inner peripheral surface of the second cylinder portion 336 are in contact with each other, and a plurality of (four in FIG. 11) recessed portions 334a is formed at equal intervals on the outer peripheral surface of the first cylinder portion 334. The gap between the recessed portions 334a and the inner peripheral surface of the second cylinder portion 336 is the element chamber inlet 327. When the element chamber inlet 327 is made up of a plurality of (four in FIG. 11) gaps in this way, the total cross-sectional area of the plurality of gaps is the total cross-sectional area B.

Figure 12:
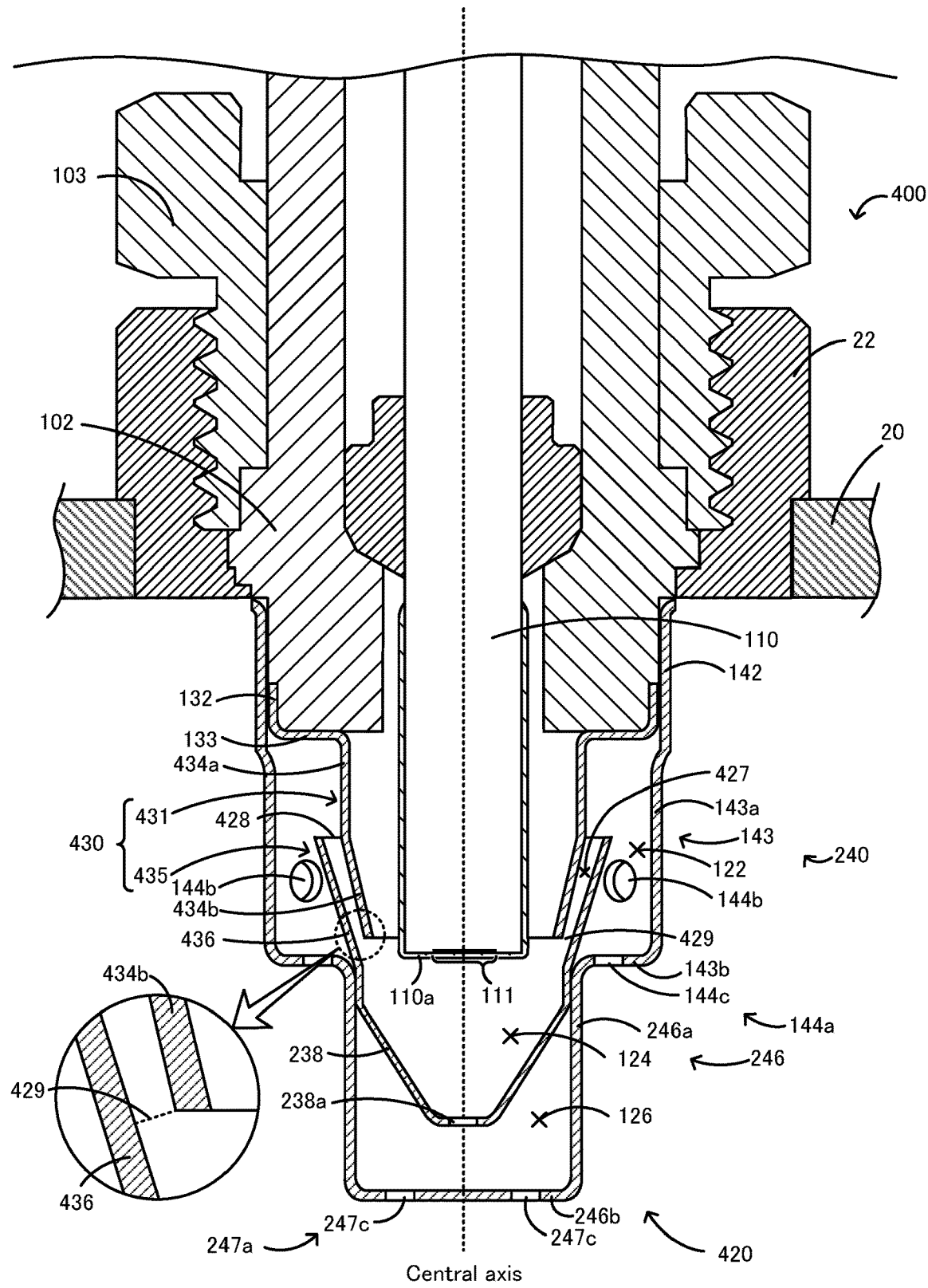
FIG. 12 is a longitudinal sectional view of a gas sensor 400 of a modification.

In the above-described embodiment, the element chamber inlet 127 is a flow channel parallel to the rear end-tip end direction of the sensor element 110 (a flow channel parallel to the up-down direction in FIG. 3); however, the configuration is not limited thereto. For example, the element chamber inlet may be a flow channel inclined at an angle with respect to the rear end-tip end direction so as to approach the sensor element 110 from the rear end side of the sensor element 110 toward the tip end side of the sensor element 110. FIG. 12 is a longitudinal sectional view of a gas sensor 400 of a modification in this case. In FIG. 12, like reference signs are assigned to the same components as those of the gas sensor 100 or the gas sensor 200, and the detailed description thereof is omitted. As shown in FIG. 12, a protective cover 420 of the gas sensor 400 includes an inner protective cover 430 instead of the inner protective cover 230. The inner protective cover 430 includes a first member 431 and a second member 435. The first member 431, as compared to the first member 131, includes a cylindrical body portion 434a and a cylindrical first cylinder portion 434b that reduces in diameter from the rear end side of the sensor element 110 toward the front side of the sensor element 110, instead of the first cylinder portion 134. The first cylinder portion 434b is connected to the body portion 434a at an end adjacent to the rear end of the sensor element 110. The second member 435, as compared to the second member 235, includes a cylindrical second cylinder portion 436 that reduces in diameter from the rear end side of the sensor element 110 toward the tip end side of the sensor element 110, instead of the second cylinder portion 136 and the connection portion 137. The second cylinder portion 436 is connected to the tip end portion 238. The outer peripheral surface of the first cylinder portion 434b and the inner peripheral surface of the second cylinder portion 436 are not in contact with each other, and the gap formed therebetween serves as an element chamber inlet 427. The element chamber inlet 427 has an outer opening 428 that is an opening adjacent to the first gas chamber 122 and an element-side opening 429 that is an opening adjacent to the sensor element chamber 124. The element chamber inlet 427 is a flow channel inclined at an angle with respect to the rear end-tip end direction so as to approach the sensor element 110 from the rear end side of the sensor element 110 toward the tip end side of the sensor element 110 (so as to approach the central axis of the inner protective cover 430) with the shapes of the first cylinder portion 434b and the second cylinder portion 436. Similarly, the element-side opening 429 is open at an angle with respect to the rear end-tip end direction so as to approach the sensor element 110 from the rear end side of the sensor element 110 toward the tip end side of the sensor element 110 (see the enlarged view in FIG. 12). When the element chamber inlet 427 is an inclined flow channel in this way or when the element-side opening 429 is open at an angle, the direction in which measurement-object gas flows out from the element-side opening 429 to the sensor element chamber 124 is a direction inclined at an angle with respect to the rear end-tip end direction of the sensor element 110. Thus, similar advantageous effects to those of the element chamber inlet 127 or the element-side opening 129 of the above-described embodiment are obtained. In other words, it is possible to reduce a situation in which measurement-object gas perpendicularly strikes the surface (surface other than the gas inlet port 111) of the sensor element 110 and to reduce a situation in which measurement-object gas passes along the surface of the sensor element 110 over a long distance and then reaches the gas inlet port 111. Thus, it is possible to suppress a decrease in the heat retaining property of the sensor element 110. In FIG. 12, the width of the element chamber inlet 427 narrows from the rear end side of the sensor element 110 toward the tip end side of the sensor element 110. Therefore, the opening area of the element-side opening 429 is less than the opening area of the outer opening 428. In other words, in the element chamber inlet 427, the distance A4 is less than the distance A5 described with reference to FIG. 7. Thus, when measurement-object gas flows in from the outer opening 428 and flows out from the element-side opening 429, the flow speed of measurement-object gas increases at the time of flowing out as compared to at the time of flowing in. Therefore, it is possible to improve the response of specific gas concentration detection. In FIG. 12, the element chamber inlet 427 is a flow channel inclined at an angle with respect to the rear end-tip end direction, of the sensor element 110, the element-side opening 429 is open at an angle with respect to the rear end-tip end direction of the sensor element 110, and the opening area of the element-side opening 429 is less than the opening area of the outer opening 428. Alternatively, one or more of these three features may be omitted, or a gas sensor may have one or more of these three features. With the thus configured gas sensor 400 as well, when the cross-sectional area ratio A/D is greater than a value of 2.0 and less than or equal to a value of 5.0, B>A>C>D is satisfied, and A×B×C×D is greater than or equal to a value of 3000 and less than or equal to a value of 8500, similar advantageous effects to those of the above-described embodiment are obtained. In the gas sensor 400 of FIG. 12, as in the case of the gas sensor 200, the tip end portion 246 of the outer protective cover 240 has a cylindrical shape without a tapered portion, and the tip end portion 238 of the inner protective cover 430 has an inverted truncated cone shape. Alternatively, the gas sensor 400 may have the tip end portion 138, the stepped portion 139, and the tip end portion 146 as in the case of the gas sensor 100.

In the above-described embodiment, the element-side opening 129 is open in the tip end direction; however, the configuration is not limited thereto. The element-side opening 129 may be open to the sensor element chamber 124, for example, in a direction perpendicular to the tip end direction. In the above-described embodiment, the element chamber inlet 127 is a flow channel parallel to the rear end-tip end direction of the sensor element 110; however, the configuration is not limited thereto. The element chamber inlet 127 may be, for example, a flow channel along a direction perpendicular to the tip end direction.

In the above-described embodiment, a flow channel for measurement-object gas between the outer inlets 144a and the element chamber inlet 127 is only the first gas chamber 122; however, the configuration is not limited thereto. It is sufficient that the first gas chamber 122 is at least part of a flow channel for measurement-object gas between the outer inlets 144a and the element chamber inlet 127. For example, the protective cover 120 may include an intermediate protective cover disposed between the inner protective cover 130 and the outer protective cover 140 in addition to the inner protective cover 130 and the outer protective cover 140, and a flow channel for measurement-object gas between the outer inlets 144a and the element chamber inlet 127 may include a plurality of gas chambers. Similarly, in the above-described embodiment, a flow channel for measurement-object gas between the outer outlet 147a and the element chamber outlets 138a is only the second gas chamber 126; however, the configuration is not limited thereto. It is sufficient that the second gas chamber 126 is at least part of a flow channel for measurement-object gas between the outer outlet 147a and the element chamber outlets 138a.

In the above-described embodiment, the inner protective cover 130 includes two members, that is, the first member 131 and the second member 135. Alternatively, the first member 131 and the second member 135 may be an integrated member.

In the above-described embodiment, the gas inlet port 111 is open at the tip end surface of the sensor element 110 (the lower surface of the sensor element 110 in FIG. 3); however, the configuration is not limited thereto. For example, the gas inlet port 111 may be open at the side surface of the sensor element 110 (the surface of the up-down and right-left direction of the sensor element 110 in FIG. 4).

In the above-described embodiment, the sensor element 110 includes the porous protective layer 110a. Alternatively, the sensor element 110 does not need to include the porous protective layer 110a.

In the above-described embodiment, the protective cover 120 is described as part of the gas sensor 100. Alternatively, the protective cover 120 may be distributed solely.

EXAMPLES

Hereinafter, specific examples of a manufactured gas sensor will be described as examples. Test Examples 4 to 7, 9, 10, 12 to 14, 18, 21, and 23 correspond to examples of the present invention, and Test Examples 1 to 3, 8, 11, 15 to 17, 19, 20, and 22 correspond to comparative examples. The present invention is not limited to the following examples.

Test Example 1

Figure 13:
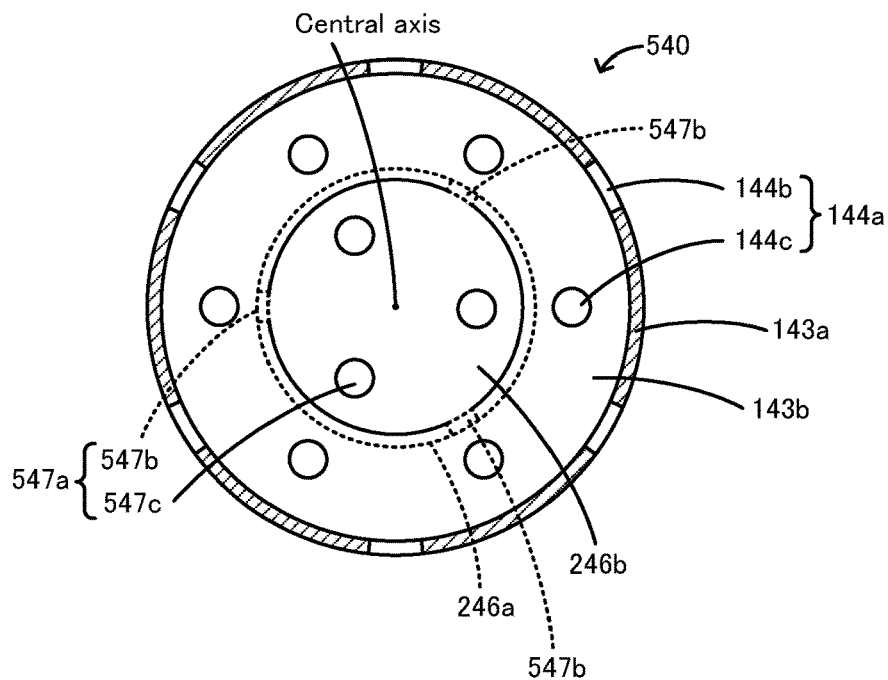
FIG. 13 is a cross-sectional view, corresponding to FIG. 9, of an outer protective cover 540 of Test Example 1.
Figure 14:
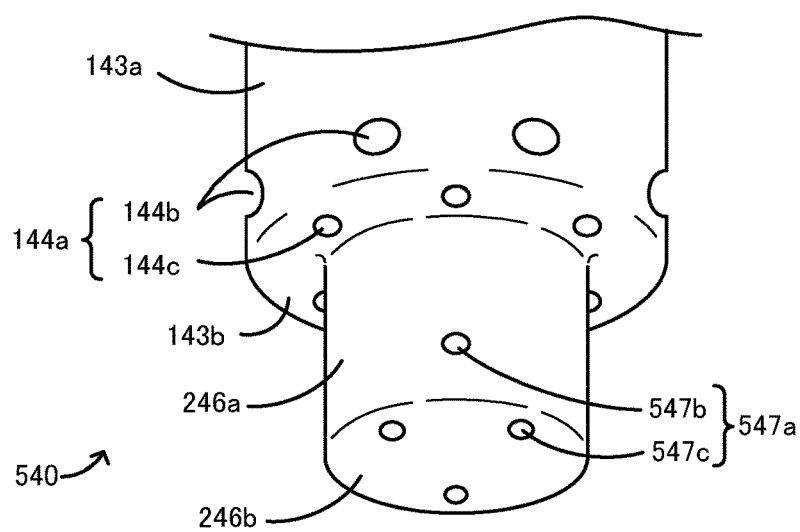
FIG. 14 is a perspective view, corresponding to FIG. 10, of a gas sensor of Test Example 1.

The gas sensor 200 shown in FIG. 8 to FIG. 10 was employed as Test Example 1 except that an outer protective cover 540 shown in FIG. 13 and FIG. 14 was used instead of the outer protective cover 240. Specifically, the first member 131 of the inner protective cover 230 was configured such that the sheet thickness was 0.3 mm, the axial length was 10.2 mm, the axial length of the large-diameter portion 132 was 1.8 mm, the outside diameter of the large-diameter portion 132 was 14.4 mm, the axial length of the first cylinder portion 134 was 8.4 mm, and the outside diameter of the first cylinder portion 134 was 8.48 mm. The second member 235 was configured such that the sheet thickness was 0.3 mm, the axial length was 11.5 mm, the axial length of the second cylinder portion 136 was 4.5 mm, the inside diameter of the second cylinder portion 136 was 9.7 mm, the axial length of the tip end portion 238 was 4.9 mm, and the diameter of the bottom surface of the tip end portion 238 was 3.0 mm. For the element chamber inlet 127, each of the distances A4, A5, A7 was set to 0.61 mm, and the distance L was set to 4 mm. The diameter of the element chamber outlet 238a was set to 1.5 mm. The outer protective cover 540 was configured such that the sheet thickness was 0.4 mm, the axial length was 24.35 mm, the axial length of the large-diameter portion 142 was 5.85 mm, the outside diameter of the large-diameter portion 142 was 15.2 mm, the axial length of the body portion 143 was 8.9 mm (the axial length from the upper end of the body portion 143 to the upper surface of the stepped portion 143b was 8.5 mm), the outside diameter of the body portion 143 was 14.6 mm, the axial length of the tip end portion 246 was 9.6 mm, and the outside diameter of the tip end portion 246 was 8.7 mm. The outer inlets 144a were configured such that the six horizontal holes 144b having a diameter of 1 mm and the six vertical holes 144c having a diameter of 1 mm were alternately formed at equal intervals (an angle formed between the adjacent holes was 30°). The outer outlets 547a were configured such that the three horizontal holes 547b having a diameter of 1 mm and the three vertical holes 547c having a diameter of 1 mm were alternately formed at equal intervals (an angle formed between the adjacent holes was 60°). The material of the protective cover 220 was SUS310S. The sensor element 110 of the gas sensor 200 was configured such that the width (the length in the right-left direction in FIG. 8) was 4 mm and the thickness (the length in a direction perpendicular to the sheet in FIG. 8) was 1.5 mm. The porous protective layer 110a was an alumina porous body, and had a thickness of 400 μm. In Test Example 1, the total cross-sectional area A was set to 9.4 mm$^2$, the total cross-sectional area B was set to 15.9 mm$^2$, the total cross-sectional area C was set to 1.8 mm$^2$, and the total cross-sectional area D was set to 4.7 mm$^2$. The cross-sectional area ratio A/D was set to a value of 2.0.

Test Example 2

The gas sensor 100 shown in FIG. 3 to FIG. 7 was assumed as Test Example 2. Specifically, the first member 131 of the inner protective cover 130 was configured such that the sheet thickness was 0.3 mm, the axial length was 10.2 mm, the axial length of the large-diameter portion 132 was 1.8 mm, the outside diameter of the large-diameter portion 132 was 14.4 mm, the axial length of the first cylinder portion 134 was 8.4 mm, and the outside diameter of the first cylinder portion 134 was 8.48 mm. The second member 135 was configured such that the sheet thickness was 0.3 mm, the axial length was 11.5 mm, the axial length of the second cylinder portion 136 was 4.5 mm, the inside diameter of the second cylinder portion 136 was 9.7 mm, the axial length of the tip end portion 138 was 4.9 mm, and the outside diameter of the side portion 138d of the tip end portion 138 was 5.6 mm. For the element chamber inlet 127, each of the distances A4, A5, A7 was set to 0.61 mm, and the distance L was set to 4 mm. The element chamber outlets 138a were configured such that the four horizontal holes 138b having a diameter of 1.5 mm were formed at equal intervals. The outer protective cover 140 was configured such that the sheet thickness was 0.4 mm, the axial length was 24.35 mm, the axial length of the large-diameter portion 142 was 5.85 mm, the outside diameter of the large-diameter portion 142 was 15.2 mm, the axial length of the body portion 143 was 8.9 mm (the axial length from the upper end of the body portion 143 to the upper surface of the stepped portion 143b was 8.5 mm), the outside diameter of the body portion 143 was 14.6 mm, the axial length of the tip end portion 146 was 9.6 mm, the axial length of the side portion 146a of the tip end portion 146 was 9.6 mm, the outside diameter of the side portion 146a of the tip end portion 146 was 8.7 mm, and the diameter of the bottom portion 146b of the tip end portion 146 was 2.6 mm. The outer inlets 144a were configured such that the six horizontal holes 144b having a diameter of 1.5 mm and the six vertical holes 144c having a diameter of 1.0 mm were alternately formed at equal intervals. The diameter of the outer outlet 147a was set to 1.0 mm. The material of the protective cover 120 was SUS310S. The sensor element 110 of the gas sensor 100 was configured such that the width (the length in the right-left direction in FIG. 4) was 4 mm and the thickness (the length in the up-down direction in FIG. 4) was 1.5 mm. The porous protective layer 110a was an alumina porous body, and had a thickness of 400 μm. In Test Example 2, the total cross-sectional area A was set to 15.3 mm$^2$, the total cross-sectional area B was set to 15.9 mm$^2$, the total cross-sectional area C was set to 7.1 mm$^2$, and the total cross-sectional area D was set to 0.8 mm$^2$. The cross-sectional area ratio A/D was set to a value of 19.1.

Test Example 3

The gas sensor 200 shown in FIG. 8 to FIG. 10 was assumed as Test Example 3. In Test Example 3, the outer outlets 247a had no horizontal hole, and included the six vertical holes 247c, and the diameter of each vertical hole 247c was set to 1.0 mm that is the same as that of Test Example 1. The diameter of each horizontal hole 144b was set to 1.5 mm. Other than that, the same dimensions as those of Test Example 1 were used. In Test Example 3, the total cross-sectional area A was set to 15.3 mm$^2$, the total cross-sectional area B was set to 15.9 mm$^2$, the total cross-sectional area C was set to 1.8 mm$^2$, and the total cross-sectional area D was set to 4.7 mm$^2$. The cross-sectional area ratio A/D was set to a value of 3.3.

Test Examples 4 to 23

Test Examples 4 to 23 were configured similarly to the gas sensor 100 of Test Example 2 except that the dimensions of the outer inlets 144a, the element chamber inlet 127, the element chamber outlets 138a, and the outer outlet 147a were adjusted such that the total cross-sectional areas A to D became the values shown in Table 1. Specifically, in Test Examples 5, 7 to 11, and 16 to 19, the six horizontal holes 144b having a diameter of 1.06 mm and the six vertical holes 144c having a diameter of 1.06 mm were alternately formed at equal intervals as the outer inlets 144a, and the total cross-sectional area A was set to 10.6 mm$^2$. In Test Examples 7, 9, 11, 15, 17, 19, 20, and 22, the outside diameter of the first cylinder portion 134 was set to 8.5 mm, the inside diameter of the second cylinder portion 136 was set to 10.7 mm, and the total cross-sectional area B was set to 31.7=$^2$. In Test Example 23, the outside diameter of the first cylinder portion 134 was set to 9.48 mm, the inside diameter of the second cylinder portion 136 was set to 11.0 mm, and the total cross-sectional area B was set to 24.4 mm$^2$. In addition, in Test Example 6, the four horizontal holes 138b having a diameter of 1.47 mm were formed at equal intervals as the element chamber outlets 138a, and the total cross-sectional area C was set to 6.8 mm$^2$. In Test Examples 8, 9, 12, and 13, the four horizontal holes 138b having a diameter of 1.14 mm were formed at equal intervals as the element chamber outlets 138a, and the total cross-sectional area C was set to 4.1 mm$^2$. In Test Examples 10, 11, 14, and 15, the four horizontal holes 138b having a diameter of 1.77 mm were formed at equal intervals as the element chamber outlets 138a, and the total cross-sectional area C was set to 9.8 mm$^2$. In Test Examples 4 to 15, and 23, the diameter of the outer outlet 147a was set to 2.0 mm, and the total cross-sectional area D was set to 3.1 mm$^2$. In Test Examples 18, 19, 21, and 22, the diameter of the outer outlet 147a was set to 2.44 mm, and the total cross-sectional area D was set to 4.7 mm².

[Evaluation of Response and Heat Retaining Property]

The gas sensors of Test Examples 1 to 23 each were connected to a pipe similarly as shown in FIG. 1 and FIG. 2. Gas obtained by adjusting the atmosphere by mixture of oxygen into a selected oxygen concentration was used as measurement-object gas, and the measurement-object gas was caused to flow in the pipe at a flow speed V of 1 m/s or a flow speed V of 10 m/s. Then, a temporal change in the output of the sensor element and a change in input power to a heater in the case where the oxygen concentration of measurement-object gas to be caused to flow in the pipe was changed from 22.9% to 20.2% were investigated. Where the output value of the sensor element just before the oxygen concentration was changed was 0% and the output value at the time when the output of the sensor element after a change of the oxygen concentration varied and then became stable was 100%, an elapsed time from when the output value exceeds 10% to when the output value exceeds 90% was defined as a response time [sec] of specific gas concentration detection. It means that the response of specific gas concentration detection increases as the response time shortens. The maximum value of input power to the heater of the sensor element from when the output value exceeded 10% to when the output value exceeded 90% was measured as heater power (W). As the flow speed steeply changes, the sensor element is more cooled and, as a result, the heater power increases, so a low heater power means that the sensor element is less likely to be cooled, that is, the heat retaining property is high. Measurement of each of a response time and a heater power was performed multiple times for each test example, and the average of each was determined as a response time and a heater power for an associated test example.

Table 1 shows the total cross-sectional areas, the cross-sectional area ratios, the response, and the heat retaining property of each of the gas sensors of Test Examples 1 to 23. In Table 1, the response time measured under the condition that the flow speed of measurement-object gas was set to 1 m/s was used to evaluate the response, and it was determined that the response was OK when the response time was shorter than or equal to three seconds. A heater power (power) measured under the condition that the flow speed of measurement-object gas was set to 60 m/s was used to evaluate the heat retaining property, and it was determined that the heat retaining property was OK when the power was lower than or equal to 10 W.

TABLE 1

| | Total cross-sectional area [mm²] | | | | Cross-sectional area ratio | | | | | Response | | Heat retaining property | |
|---|---|---|---|---|---|---|---|---|---|---|---|---|---|
| | | | | | | | | | | Response time | Evaluation | Power | Evaluation |
| | A | B | C | D | B/A | A/C | C/D | A/D | A × B × C × D | [s] | (≤3 s) | [W] | (≤10 W) |
| Test Example 1 | 9.4 | 15.9 | 1.8 | 4.7 | 1.7 | 5.2 | 0.4 | 2.0 | 1264 | 6.40 | NG | 8.37 | OK |
| Test Example 2 | 15.3 | 15.9 | 7.1 | 0.8 | 1.0 | 2.2 | 8.9 | 19.1 | 1382 | 6.19 | NG | 8.20 | OK |
| Test Example 3 | 15.3 | 15.9 | 1.8 | 4.7 | 1.0 | 8.5 | 0.4 | 3.3 | 2058 | 3.53 | NG | 8.96 | OK |
| Test Example 4 | 15.3 | 15.9 | 7.1 | 3.1 | 1.0 | 2.2 | 2.3 | 4.9 | 5354 | 2.21 | OK | 9.04 | OK |
| Test Example 5 | 10.6 | 15.9 | 7.1 | 3.1 | 1.5 | 1.5 | 2.3 | 3.4 | 3710 | 2.60 | OK | 8.84 | OK |
| Test Example 6 | 15.3 | 15.9 | 6.8 | 3.1 | 1.0 | 2.3 | 2.2 | 4.9 | 5128 | 2.37 | OK | 8.83 | OK |
| Test Example 7 | 10.6 | 31.7 | 7.1 | 3.1 | 3.0 | 1.5 | 2.3 | 3.4 | 7396 | 1.80 | OK | 8.83 | OK |
| Test Example 8 | 10.6 | 15.9 | 4.1 | 3.1 | 1.5 | 2.6 | 1.3 | 3.4 | 2142 | 4.20 | NG | 8.30 | OK |
| Test Example 9 | 10.6 | 31.7 | 4.1 | 3.1 | 3.0 | 2.6 | 1.3 | 3.4 | 4271 | 2.50 | OK | 8.60 | OK |
| Test Example 10 | 10.6 | 15.9 | 9.8 | 3.1 | 1.5 | 1.1 | 3.2 | 3.4 | 5120 | 2.20 | OK | 8.80 | OK |
| Test Example 11 | 10.6 | 31.7 | 9.8 | 3.1 | 3.0 | 1.1 | 3.2 | 3.4 | 10208 | 1.00 | OK | 10.30 | NG |
| Test Example 12 | 15.3 | 15.9 | 4.1 | 3.1 | 1.0 | 3.7 | 1.3 | 4.9 | 3092 | 3.00 | OK | 8.50 | OK |
| Test Example 13 | 15.3 | 31.7 | 4.1 | 3.1 | 2.1 | 3.7 | 1.3 | 4.9 | 6164 | 1.90 | OK | 9.20 | OK |
| Test Example 14 | 15.3 | 15.9 | 9.8 | 3.1 | 1.0 | 1.6 | 3.2 | 4.9 | 7391 | 1.60 | OK | 9.40 | OK |
| Test Example 15 | 15.3 | 31.7 | 9.8 | 3.1 | 2.1 | 1.6 | 3.2 | 4.9 | 14735 | 0.80 | OK | 11.00 | NG |
| Test Example 16 | 10.6 | 15.9 | 7.1 | 0.8 | 1.5 | 1.5 | 8.9 | 13.3 | 957 | 6.00 | NG | 8.20 | OK |
| Test Example 17 | 10.6 | 31.7 | 7.1 | 0.8 | 3.0 | 1.5 | 8.9 | 13.3 | 1909 | 3.50 | NG | 8.50 | OK |
| Test Example 18 | 10.6 | 15.9 | 7.1 | 4.7 | 1.5 | 1.5 | 1.5 | 2.3 | 5624 | 2.00 | OK | 8.80 | OK |
| Test Example 19 | 10.6 | 31.7 | 7.1 | 4.7 | 3.0 | 1.5 | 1.5 | 2.3 | 11213 | 0.95 | OK | 10.50 | NG |
| Test Example 20 | 15.3 | 31.7 | 7.1 | 0.8 | 2.1 | 2.2 | 8.9 | 19.1 | 2755 | 3.20 | NG | 8.40 | OK |
| Test Example 21 | 15.3 | 15.9 | 7.1 | 4.7 | 1.0 | 2.2 | 1.5 | 3.3 | 8118 | 1.40 | OK | 9.60 | OK |
| Test Example 22 | 15.3 | 31.7 | 7.1 | 4.7 | 2.1 | 2.2 | 1.5 | 3.3 | 16185 | 0.78 | OK | 11.30 | NG |
| Test Example 23 | 15.3 | 24.4 | 7.1 | 3.1 | 1.6 | 2.2 | 2.3 | 4.9 | 8323 | 1.33 | OK | 9.80 | OK |

As shown in Table 1, it is found that both the response and the heat retaining property were OK in Test Examples 4 to 7, 9, 10, 12 to 14, 18, 21, and 23 in which the total cross-sectional areas A to D satisfy B>A>C>D (in Table 1, B/A>1, A/C>1, and C/D>1 all are satisfied), the total cross-sectional area ratio A/D is greater than a value of 2.0 and less than or equal to a value of 5.0, and A×B×C×D is greater than or equal to a value of 3000 and less than or equal to a value of 8500. Specifically, the response is low in Test Example 1 in which the value of A/D is less than or equal to 2.0 and in Test Examples 2, 16, 17, and 20 in which the value of A/D is greater than 5.0, so it is presumable that A/D needs to be greater than a value of 2.0 and less than or equal to 5.0 in order to enhance the response. The response is low in Test Examples 1 and 3 in which C/D is less than or equal to a value of 1, that is, C D, so it is presumable that C>D needs to be satisfied in order to enhance the response. In addition, when the test examples having the same values of C/D and A/C and having different values of only B/A, that is, Test Examples 2 and 20, Test Examples 4 and 23, Test Examples 5 and 7, Test Examples 8 and 9, Test Examples 10 and 11, Test Examples 12 and 13, Test Examples 14 and 15, Test Examples 16 and 17, Test Examples 18 and 19, and Test Examples 21 and 22 are compared with each other, it is observed that the response tends to decrease as the value of B/A reduces. Since the test example having the smallest value of B/A has B/A greater than a value of 1, it is inferred that B/A needs to be greater than a value of 1, that is, B>A needs to be satisfied, in order to enhance the response. In addition, test examples having the same value of B/A and different values of A/C, that is, Test Examples 3 and 21, Test Examples 4, 6, 12, and 14, Test Examples 5, 8, and 10, Test Examples 7, 9, and 11, and Test Examples 13 and 15 are compared with each other, it is observed that the heat retaining property tends to decrease as the value of A/C reduces. Since the test example having the smallest value of A/C has A/C greater than a value of 1, it is inferred that A/C needs to be greater than a value of 1, that is, A>C needs to be satisfied, in order to enhance the heat retaining property. Even when the above-described all conditions are satisfied, the response is low in Test Example 8 in which the value of A×B×C×D is less than 3000, so it is presumable that the value of A×B×C×D needs to be greater than or equal to 3000 in order to enhance the response. The heat retaining property is low in Test Examples 11, 15, 19, and 22 in which the value of A×B×C×D is greater than 8500, so it is presumable that the value of A×B×C×D needs to be less than or equal to 8500 in order to enhance the heat retaining property.

What is claimed is:

1. A gas sensor comprising:
   a sensor element having a gas inlet port that introduces measurement-object gas and capable of detecting a specific gas concentration of the measurement-object gas having flowed in from the gas inlet port;
   an inner protective cover having inside a sensor element chamber in which a tip end of the sensor element and the gas inlet port are disposed, and having one or more element chamber inlets that are inlets to the sensor element chamber and one or more element chamber outlets that are outlets from the sensor element chamber; and
   an outer protective cover disposed outside the inner protective cover and having one or more outer inlets that are inlets for the measurement-object gas from an outside and one or more outer outlets that are outlets for the measurement-object gas to the outside,
   wherein the outer protective cover and the inner protective cover form, as spaces between the outer protective cover and the inner protective cover, a first gas chamber that is at least part of a flow channel for the measurement-object gas between the one or more outer inlets and the one or more element chamber inlets and a second gas chamber that is at least part of a flow channel for the measurement-object gas between the one or more outer outlets and the one or more element chamber outlets and that does not directly communicate with the first gas chamber, and
   a total cross-sectional area A [mm$^2$] of the one or more outer inlets, a total cross-sectional area B [mm$^2$] of the one or more element chamber inlets, a total cross-sectional area C [mm$^2$] of the one or more element chamber outlets, and a total cross-sectional area D [mm$^2$] of the one or more outer outlets satisfy B>A>C>D, a cross-sectional area ratio A/D that is a ratio between the total cross-sectional area A and the total cross-sectional area D is greater than a value of 2.0 and less than or equal to a value of 5.0, and A×B×C×D that is a product of the total cross-sectional areas A to D is greater than or equal to a value of 3000 and less than or equal to a value of 8500.

2. The gas sensor according to claim 1,
   wherein the cross-sectional area ratio A/D is greater than or equal to a value of 2.5.
3. The gas sensor according to claim 1,
   wherein one or more of a condition in which the total cross-sectional area A is greater than or equal to 10 mm$^2$ and less than or equal to 30 mm$^2$, a condition in which the total cross-sectional area B is greater than or equal to 15 mm$^2$ and less than or equal to 50 mm$^2$, a condition in which the total cross-sectional area C is greater than or equal to 5 mm$^2$ and less than or equal to 15 mm$^2$, and a condition in which the total cross-sectional area D is greater than or equal to 1.6 mm$^2$ and less than or equal to 10 mm$^2$ are satisfied.
4. The gas sensor according to claim 1,
   wherein the outer protective cover has a closed-end cylindrical shape and has a side portion and a bottom portion, and
   the one or more outer outlets are not disposed at the side portion of the outer protective cover.
5. The gas sensor according to claim 1,
   wherein the inner protective cover has a closed-end cylindrical shape and has a side portion and a bottom portion, and
   the one or more element chamber outlets are not disposed at the bottom portion of the inner protective cover.
6. The gas sensor according to claim 1,
   wherein the inner protective cover forms the one or more element chamber inlets such that, where a direction from a rear end of the sensor element toward the tip end is a tip end direction, an element-side opening that is an opening adjacent to the sensor element chamber of each of the one or more element chamber inlets is open in the tip end direction.
7. The gas sensor according to claim 1,
   wherein the inner protective cover has a first member and a second member, and
   the first member and the second member form the one or more element chamber inlets as a gap between the first member and the second member.
8. The gas sensor according to claim 7,
   wherein the first member has a first cylinder portion surrounding the sensor element,
   the second member has a second cylinder portion larger in diameter than the first cylinder portion, and
   the one or more element chamber inlets are a cylindrical gap between an outer peripheral surface of the first cylinder portion and an inner peripheral surface of the second cylinder portion.
9. A protective cover for protecting a sensor element having a gas inlet port that introduces measurement-object gas and capable of detecting a specific gas concentration of the measurement-object gas that has flowed in from the gas inlet port, the protective cover comprising:
   an inner protective cover having inside a sensor element chamber for disposing a tip end of the sensor element and the gas inlet port inside, and having one or more element chamber inlets that are inlets to the sensor element chamber and one or more element chamber outlets that are outlets from the sensor element chamber; and
   an outer protective cover disposed outside the inner protective cover and having one or more outer inlets that are inlets for the measurement-object gas from an outside and one or more outer outlets that are outlets for the measurement-object gas to the outside, wherein
   the outer protective cover and the inner protective cover form, as spaces between the outer protective cover and the inner protective cover, a first gas chamber that is at least part of a flow channel for the measurement-object gas between the one or more outer inlets and the one or more element chamber inlets and a second gas chamber that is at least part of a flow channel for the measurement-object gas between the one or more outer outlets and the one or more element chamber outlets and that does not directly communicate with the first gas chamber, and a total cross-sectional area A [mm$^2$] of the one or more outer inlets, a total cross-sectional area B [mm$^2$] of the one or more element chamber inlets, a total cross-sectional area C [mm$^2$] of the one or more element chamber outlets, and a total cross-sectional area D [mm$^2$] of the one or more outer outlets satisfy B>A>C>D, a cross-sectional area ratio A/D that is a ratio between the total cross-sectional area A and the total cross-sectional area D is greater than a value of 2.0 and less than or equal to a value of 5.0, and A×B×C×D that is a product of the total cross-sectional areas A to D is greater than or equal to a value of 3000 and less than or equal to a value of 8500.

\* \* \* \* \*